US012758306B2

(12) United States Patent
Godara et al.

(10) Patent No.: US 12,758,306 B2
(45) Date of Patent: Oct. 13, 2026

(54) ELECTROSURIGCAL DEVICE AND METHODS

(71) Applicant: Baylis Medical Technologies Inc., Mississauga (CA)

(72) Inventors: Neil Godara, Milton (CA); Robert Harrison, Norval (CA); Ahmad Dastjerdi, Toronto (CA); Abelardo Escoto, Toronto (CA); Aaron Peng, Surrey (CA); Andrew Oldham, Georgetown (CA); Jimmy Huynh, York (CA); Ryan Li, Barrie (CA)

(73) Assignee: Baylis Medical Technologies Inc., Mississauga (CA)

( * ) Notice: Subject to any disclaimer, the term of this patent is extended or adjusted under 35 U.S.C. 154(b) by 701 days.

(21) Appl. No.: 18/026,025

(22) PCT Filed: Sep. 14, 2021

(86) PCT No.: PCT/IB2021/058377
§ 371 (c)(1),
(2) Date: Mar. 13, 2023

(87) PCT Pub. No.: WO2022/054032
PCT Pub. Date: Mar. 17, 2022

(65) Prior Publication Data

US 2024/0016538 A1 Jan. 18, 2024

Related U.S. Application Data

(60) Provisional application No. 63/077,952, filed on Sep. 14, 2020.

(51) Int. Cl.
*A61B 18/14* (2006.01)
*A61B 18/00* (2006.01)

(52) U.S. Cl.
CPC ........ *A61B 18/148* (2013.01); *A61B 18/1477* (2013.01); *A61B 2018/00011* (2013.01);
(Continued)

(58) Field of Classification Search
CPC .............. A61B 18/1477; A61B 18/148; A61B 2018/00011; A61B 2018/00023;
(Continued)

(56) References Cited

U.S. PATENT DOCUMENTS 5,334,193 A * 8/1994 Nardella ............ A61B 18/1492 606/41
5,383,876 A 1/1995 Nardella
(Continued)

FOREIGN PATENT DOCUMENTS

WO 2007002004 A2 1/2007
WO 2011123490 A1 10/2011
(Continued)

OTHER PUBLICATIONS

PCT Application No. PCT/IB2021/058377, International Report on Patentability, issue date Mar. 7, 2023.
(Continued)

*Primary Examiner* — Michael F Peffley
(74) *Attorney, Agent, or Firm* — Nir Lifshitz

(57) ABSTRACT

A method and apparatus are disclosed for a probe for forming a lesion in a target tissue. The probe comprises an elongate member with a distal tip and a proximal end. The elongate member defines a lumen therebetween which circulates cooling fluid. The probe further includes at least one active portion configured to deliver energy to the target tissue and at least one orifice. A portion of the cooling fluid is ejected from the at least one orifice to cool the target tissue and the remainder is internally circulated through the lumen of the probe.

8 Claims, 24 Drawing Sheets

(52) U.S. Cl.
CPC ............... *A61B 2018/00577* (2013.01); *A61B 2018/00702* (2013.01); *A61B 2018/00821* (2013.01); *A61B 2018/00875* (2013.01)

(58) Field of Classification Search
CPC A61B 2018/00029; A61B 2018/00577; A61B 2018/00702; A61B 2018/00821; A61B 2018/00875
See application file for complete search history.

(56) References Cited

U.S. PATENT DOCUMENTS

| | | | | |
|---|---|---|---|---|
| 5,423,811 | A * | 6/1995 | Imran | A61B 18/1492 606/41 |
| 5,913,854 | A | 6/1999 | Maguire et al. | |
| 5,951,546 | A * | 9/1999 | Lorentzen | A61B 18/1482 606/49 |
| 5,957,961 | A | 9/1999 | Maguire et al. | |
| 6,016,809 | A | 1/2000 | Mulier et al. | |
| 6,053,937 | A | 4/2000 | Edwards et al. | |
| 6,120,476 | A * | 9/2000 | Fung | A61M 25/0147 604/95.04 |
| 6,171,275 | B1 | 1/2001 | Webster, Jr. | |
| 6,217,576 | B1 * | 4/2001 | Tu | A61B 18/1492 606/41 |
| 6,466,818 | B1 | 10/2002 | Moaddeb et al. | |
| 6,575,969 | B1 | 6/2003 | Rittman, III et al. | |
| 7,303,558 | B2 | 12/2007 | Swanson | |
| 8,128,620 | B2 | 3/2012 | Wang et al. | |
| 8,353,907 | B2 | 1/2013 | Winkler et al. | |
| 8,523,930 | B2 | 9/2013 | Saunders et al. | |
| 8,882,755 | B2 | 11/2014 | Leung et al. | |
| 9,510,853 | B2 * | 12/2016 | Aljuri | A61B 34/10 |
| 10,493,172 | B2 * | 12/2019 | Lakshmanan | A61K 49/0093 |
| 2004/0019350 | A1 | 1/2004 | O'brien et al. | |
| 2006/0184165 | A1 | 8/2006 | Webster, Jr. et al. | |
| 2007/0027449 | A1 | 2/2007 | Godara et al. | |
| 2008/0091193 | A1 | 4/2008 | Kauphusman et al. | |
| 2009/0125017 | A1 | 5/2009 | Wang et al. | |
| 2009/0287206 | A1 * | 11/2009 | Jun | A61B 18/1477 606/49 |
| 2009/0312756 | A1 | 12/2009 | Schlesinger et al. | |
| 2014/0276200 | A1 * | 9/2014 | Brannan | A61B 18/1815 600/562 |
| 2019/0357959 | A1 | 11/2019 | Hou et al. | |

FOREIGN PATENT DOCUMENTS

| | | | |
|---|---|---|---|
| WO | 2013130655 | A1 | 9/2013 |
| WO | 2015192018 | A1 | 12/2015 |
| WO | 2017201504 | A1 | 11/2017 |
| WO | 2018148561 | A1 | 8/2018 |

OTHER PUBLICATIONS

PCT Application No. PCT/IB2021/058377, International Search Report, mailed Dec. 17, 2021.
PCT Application No. PCT/IB2021/058377, Written Opinion, mailed Dec. 17, 2021.
European application 21866205.4, European Search Report, Aug. 27, 2024.

* cited by examiner

ELECTROSURIGCAL DEVICE AND METHODS

TECHNICAL FIELD

The disclosure relates to the field of medical devices, and, in particular, relates to the field of pain management using high frequency electrical signals.

BACKGROUND OF THE ART

Chronic pain is commonly defined as pain lasting longer than 3 months. Chronic pain may result from an illness, be caused by an initial injury and in many cases, has no clear cause. The quality of the patient's life can be reduced as the levels of pain increase.

Additional health problems may arise due to chronic pain such as sleep disturbance, limitation in movement, strength and stamina, depression, anxiety, and fatigue. When chronic pain is localized, it may be connected to a particular nerve or set of nerves.

Radiofrequency ablation (RFA) has been shown to relieve localized pain in many patients. RFA can also be used to ablate tumors or dysfunctional tissue. RFA uses the heat generated through an ionic heating mechanism; the electrical current produced by a radio wave is used to target a nerve tissue. A generator creates a radiofrequency (RF) signal which travels to one or more electrodes placed in the patient's body. The adjacent tissue is heated as a result of the resistance to the RF current at the electrode tip. The increase in tissue temperature causes a lesion. The thermally affected area is called the thermal ablation zone. When the nerve is in the thermal ablation zone, the nerve is thermally ablated and a lesion on the nerve results in RF neurotomy (cutting of nerve signals) and blocks the pain signals.

The extent and duration of relief may depend on the level of ablation of the problem nerve. This ablation level relies on the devices, systems, and methods of the RFA. Improvements in these areas may increase the duration and level of pain relief in patients and result in improved patient outcomes.

SUMMARY

In one broad aspect, the present inventors have discovered an apparatus for forming a lesion via energy delivery while delivering cooling fluid to the target tissue. A probe comprises an elongate member with a distal tip and a proximal end and a lumen extending therebetween. At least one active portion is configured for delivering energy to the target tissue and the at least one active portion is positioned along the elongate member. The probe further comprises at least one orifice for ejecting cooling fluid to the tissue. The probe is configured such that a portion of the cooling fluid is ejected from the at least one orifice to cool the target tissue and a remainder of the cooling fluid is internally circulated through the lumen.

In another broad aspect of the present invention, a probe for forming a lesion in tissue while delivering a target tissue comprises an elongate member with a distal tip and a proximal end. A protrusion protrudes from the distal tip of the elongate member and a lumen extends between the proximal end of the elongate member and the protrusion. The probe further includes at least one active portion configured for delivering energy to the target tissue and includes at least one orifice. A portion of the cooling fluid is ejected from the at least one orifice to cool the target tissue while a remainder of the cooling fluid is circulated through the lumen.

In another broad aspect of the present invention, the present inventors have discovered a system for forming a lesion in tissue. The system comprises a probe in accordance with the present invention, a cooling pump configured to deliver the cooling fluid to the probe, and a generator configured to deliver energy to the probe.

In another broad aspect of the present invention, the inventors have discovered a method of lesioning a target tissue. The method involves the steps of inserting the probe in accordance with the present invention, positioning the at least one active portion of the probe at the target tissue, delivering energy to form a lesion, and delivering a portion of the cooling fluid to the target tissue.

In another broad aspect of the present invention, the inventors have discovered a method of delivering energy to a region of tissue within a patient's body using a medical treatment system. The medical treatment system includes an energy delivery device. The energy delivery device has a lumen for circulating fluid at a flow rate and at least one orifice. The energy delivery device is coupled to an energy source and a fluid source. The method, in accordance with the present invention, includes the steps of delivering energy through the energy delivery device and circulating fluid through the lumen of the energy delivery device, wherein a portion of the fluid is ejected from the at least one orifice.

In another broad aspect of the present invention, the inventors have discovered a method of delivering energy to a region of tissue. The method, in accordance with the present invention, comprises the steps of stimulating the region of tissue, monitoring an energy delivery parameter associated with the delivery of energy by the medical treatment system, comparing the energy delivery parameter to a predetermined energy delivery parameter, and delivering energy through the energy delivery device.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
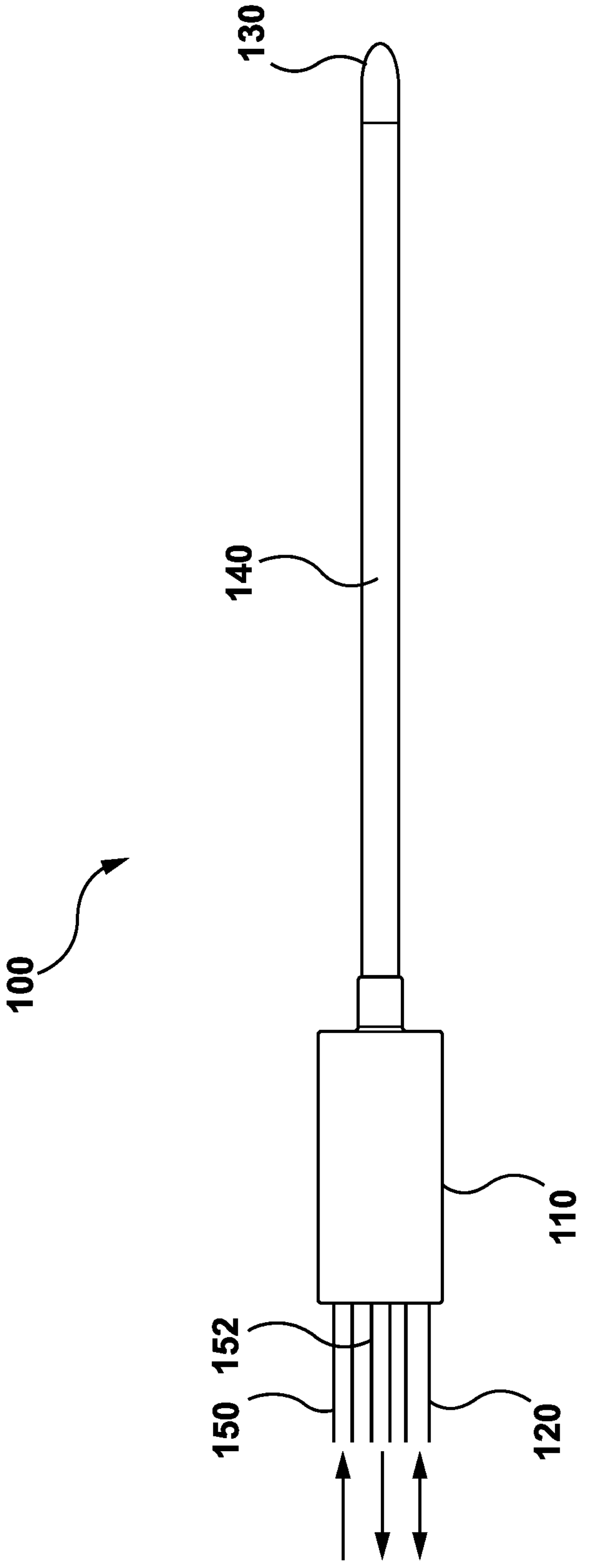
FIG. 1 is an illustration of an ablation probe in accordance with an embodiment of the present invention.

In radiofrequency ablation (RFA) procedures, the success rate for pain management depends on the size of the thermal ablation zone, as well as proper placement of the ablation probe (e.g., adjacent the target tissue). A way to increase the size of the thermal ablation zone is to increase the output of RF power. However, simply increasing output power has its own limitations: as power increases, the tissue temperature also increases which may lead to cavitation, charring or uncontrolled lesion formation. Conventional (standard) RF ablation probes additionally have inadequate distal projection of the lesion.

One means of increasing lesion size as well as lesion distal projection is employing cooling fluid in internally cooled RF probes. The cooling fluid acts as a heat sink, drawing heat away from the probe's active tip and thus lowering the temperature of nearby tissue. The temperature reduction reduces the risk of tissue cavitation and charring. By reducing the temperature of the tissue in closest proximity to the electrode, and thereby reducing the risks associated with high temperatures, the energy output and/or procedure time can be increased. The cooling allows for a prolonged application of RF and the distribution of elevated temperatures from the probe's active tip is increased which results in an increase in lesion size and distal projection (distance of lesion formation from the electrode). An aspect of the lesioning process is measuring and monitoring the temperature of the thermal ablation zone (i.e., the area being ablated). Real-time measuring and monitoring of tissue temperature allows for immediate adjustments in the amount RF energy being delivered. This in turn reduces the risk of charring and cavitation of the tissue as a result of prolonged exposure to exceedingly high temperatures.

Another means of increasing lesion size and distal projection is by applying cooling fluid directly to target tissue via an open irrigation system. In some patients or in some anatomical ablation targets, target tissue is less thermally conductive (i.e., tissues with less hydration or tissues types with higher levels of low conductivity elements such as fats, bones, ligaments) which results in a more rapid increase in proximal tissue temperatures adjacent to the probe, leading, in some cases, to an undesired lesion size and shape (for example, the lesion may have an irregular shape or the size may be smaller than desired). In an embodiment with open irrigation, the probe comprises at least one opening in the tip to allow cooling fluid to be ejected from the distal tip of the probe and applied directly to the tissue, thereby increasing the thermal and/or electrical conductivity of the tissue. In some embodiments, the cooling fluid may comprise of saline, anesthetic, contrast agents, and hydrochloric acid, or a combination thereof.

During ablation, tissue becomes less amenable (i.e., undergoes charring). When a tissue desiccates due to heating, both thermal and electrical properties rapidly change, creating a challenge for further lesion formation. By cooling and/or hydrating the tissue, these changes are slowed or prevented. Current RF ablation probes do not allow for the modulation or altering of tissue characteristics such as heat capacitance, thermal diffusivity, thermal conductivity, impedance, and/or electrical conductivity throughout the procedure. As such, the inventors have identified a need to provide a hybrid solution to allow for patient-specific modulation of tissue properties during cooling of proximate tissues during RFA.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Irrigated RF Ablation Probe

FIG. 1 illustrates one embodiment of a system and method according to the present invention comprising a device for forming a lesion such as a probe 100. The probe is inserted through the skin to the target site where soft tissue is to be lesioned. The probe has a hub 110 at its proximal end which accommodates an electrical connection to the generator (not shown). In the embodiment of FIG. 1, the generator is connected to the probe hub 110 by wire 120. The generator supplies the probe with high frequency energy such as radiofrequency (RF) which is transmitted to the exposed distal end (distal tip) 130 of the probe 100 at the target site. The high frequency energy (or "the output of high frequency energy") heats the tissue at the target site and forms a lesion by thermal ablation. The probe 100 is insulated along its shaft 140 to prevent ablation outside of the target site. In some embodiments, the probe 100 may comprise a conductive shaft and further comprises an insulating layer. In this embodiment, energy is delivered via at least one active portion (e.g., an exposed portion of the conductive shaft). In another embodiment, the probe 100 may comprise a non-conductive shaft 140, energy is delivered via a conductive wire, coupled to the active portion located on the probe 100. In this embodiment, the conductive wire would couple the active portion (e.g., an electrode) to the RF generator. A monopolar device (a device with a single active portion and/or electrode) is used with a return electrode such as a grounding pad. The return electrode is placed in conductive contact with skin and is connected to the generator. The return electrode completes the electrical circuit for the high frequency energy through the patient's body.

Figure 2A:
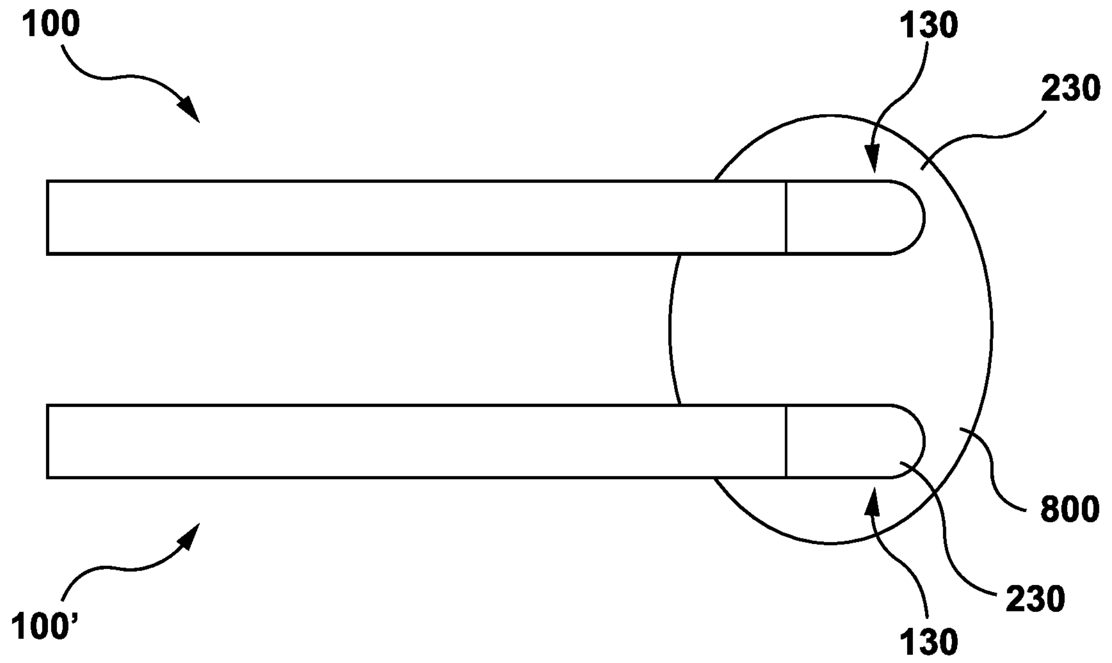
FIGS. 2*a*-2*b* illustrates the use of a secondary probe to create a return path for the energy and form a lesion therebetween in accordance with an embodiment of the present invention.
Figure 2B:
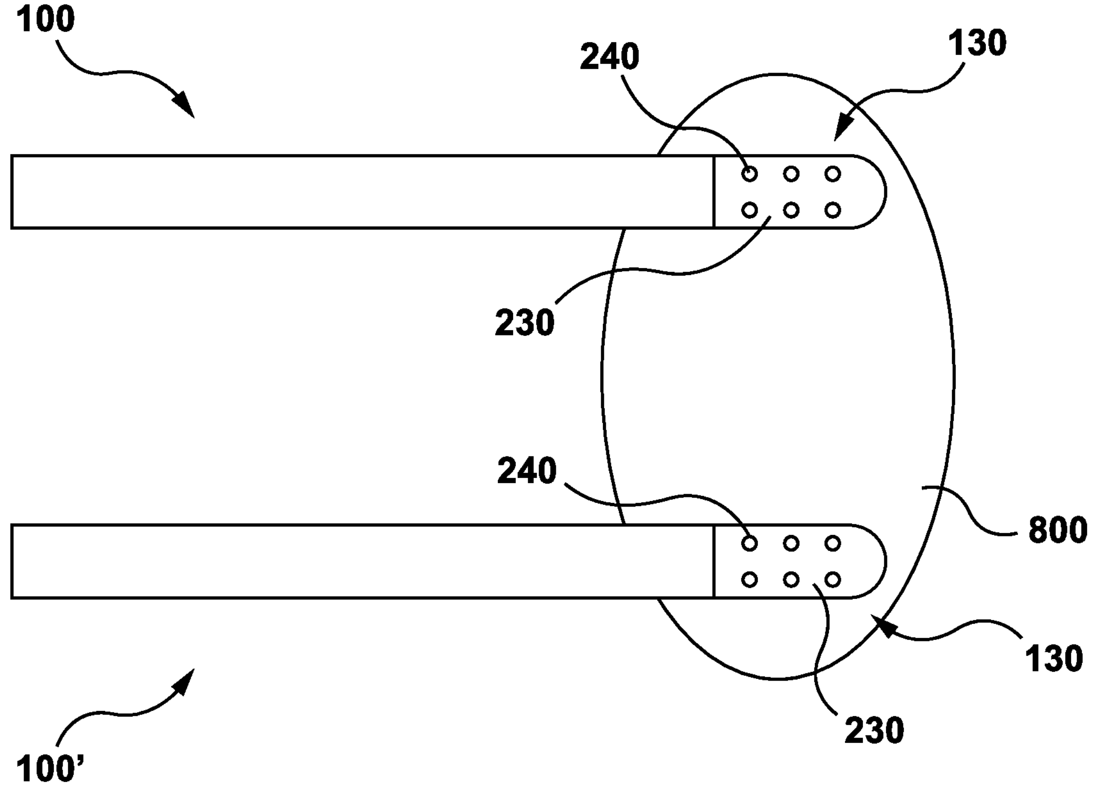

In some embodiments, the return electrode may comprise a secondary probe 100'. In one embodiment, the secondary probe 100' may be a monopolar probe (wherein the electrode 230 at the distal end 130 acts as a return electrode), as depicted in FIGS. 2A and 2B. In this configuration, each probe 100 and 100' forms a lesion that, when placed in proximity, will merge, forming a single lesion 800 between the two probes 100 and 100'. FIG. 2A illustrates the lesion 800 formed between two non-irrigated, non-cooled probes 100 and 100'. FIG. 2B depicts the lesion 800 formed between irrigated cooled probes 100 and 100' of the present invention. The cooled probes have orifices 240, described in more detail below. In both FIGS. 2A and 2B the secondary probe 100' provides a return path for the electrical circuit. As illustrated in FIG. 2A, non-irrigated cooled probes and/or standard probes must be placed closer together compared to the irrigated cooled probes (as depicted in FIG. 2B). The lesion 800 formed between non-irrigated cooled probes or standard probes are smaller compared to the lesion 800 formed between irrigated cooled probes, and thus the probes of FIG. 2A must be placed closer together to link the two lesions. In an alternative embodiment, more than two probes may be used to create the lesion between the plurality of probes.

Figure 2C:
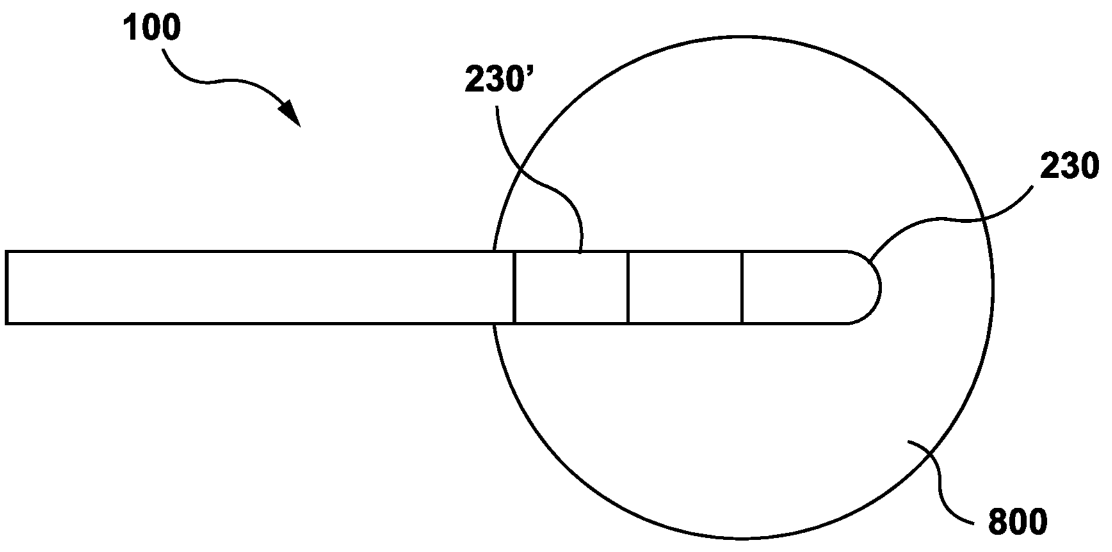
FIGS. 2*c*-2*d* illustrates a bipolar probe with a secondary active portion to create a return path for the energy and form a lesion in accordance with an embodiment of the present invention.
Figure 2D:
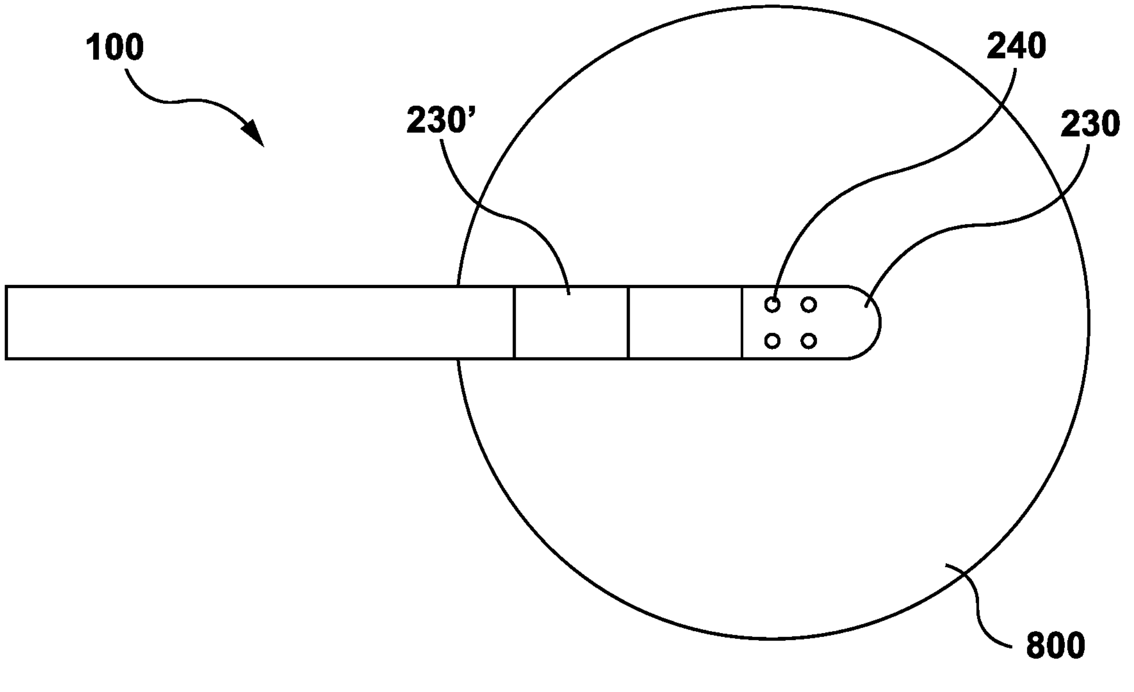

In another embodiment, at least one additional electrode 230' may be positioned along the body of the probe 100, forming a coaxial, bipolar, probe (as seen in FIGS. 2C-2D). In some embodiments, the at least one additional electrode 230' may comprise at least one orifice 240 (forming additional irrigating sections) as described later in this application. In some embodiments, at least one electrode on the probe 100 comprises at least one orifice. FIGS. 2C-2D illustrate an exemplary lesion 800 formed when using a coaxial, bipolar, probe. A larger lesion may be formed when using an irrigated cooled probe (as depicted in FIG. 2D) compared to a lesion formed with a standard probe (as seen in FIG. 2C). As further discussed below, the introduction of cooling fluid to the tissue allows for a prolonged application of RF and/or allows the user to deliver higher amounts of RF power, which in turn enables the formation of larger lesions.

With reference again to FIG. 1, the hub 110 also provides a connection to a cooling pump (not shown) through cooling tubes 150 and 152. The probe illustrated in FIG. 1 has a shaft 140 which defines a lumen for circulating fluid. In some embodiments, the fluid may be visualized on various imaging systems, such as ultrasound and/or fluoroscopy. In a specific example, the fluid may contain bubbles such that it is detectable on ultrasound systems. In another example, the fluid may contain a contrast agent which is detectable on fluoroscopy systems. In a further example, the fluid may contain both bubbles and a contrasting agent. Visualization of the fluid provides users information regarding the dispersion of fluid once it is injected into the body, thereby informing the user on positioning/location of the distal tip 130. For example, if the fluid is immediately dispersed, it may indicate to the user that the probe 100 is positioned within a blood vessel. The inlet cooling tube 150 connects the outlet of the pump to the fluid inlet lumen (not shown) within the probe hub 110. The outlet cooling tube 152 connects the fluid return lumen (not shown) within the probe hub 110 to the inlet pump. In some embodiments, the return fluid is returned to the reservoir which, in combination with additional supply, replenishes the fluid which is delivered to the target tissue.

Figure 3:
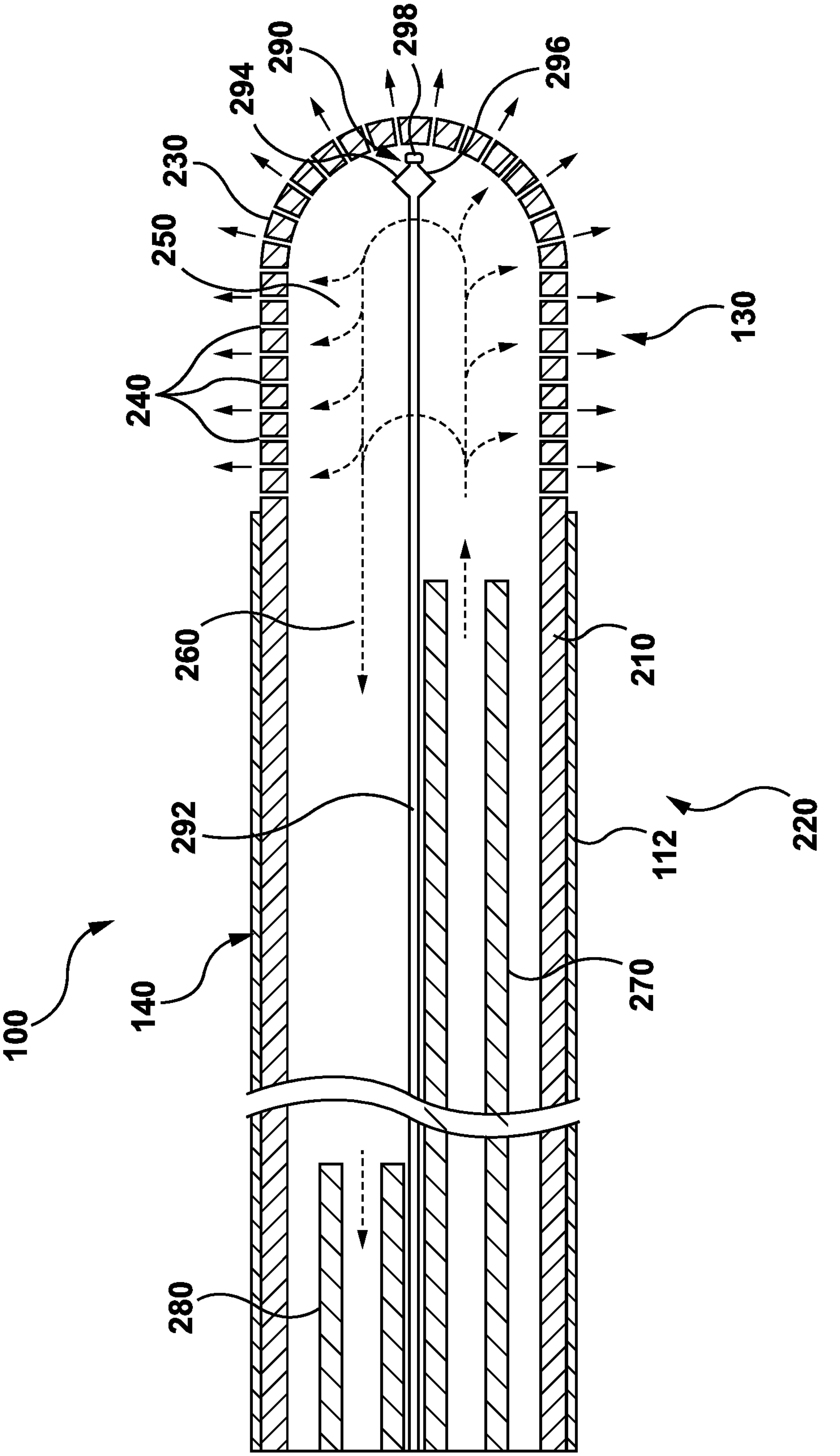
FIG. 3 is an illustration of a cut-away view of an ablation probe in accordance with an embodiment of the present invention.
Figures 4A, 4B, 4C, 4D:
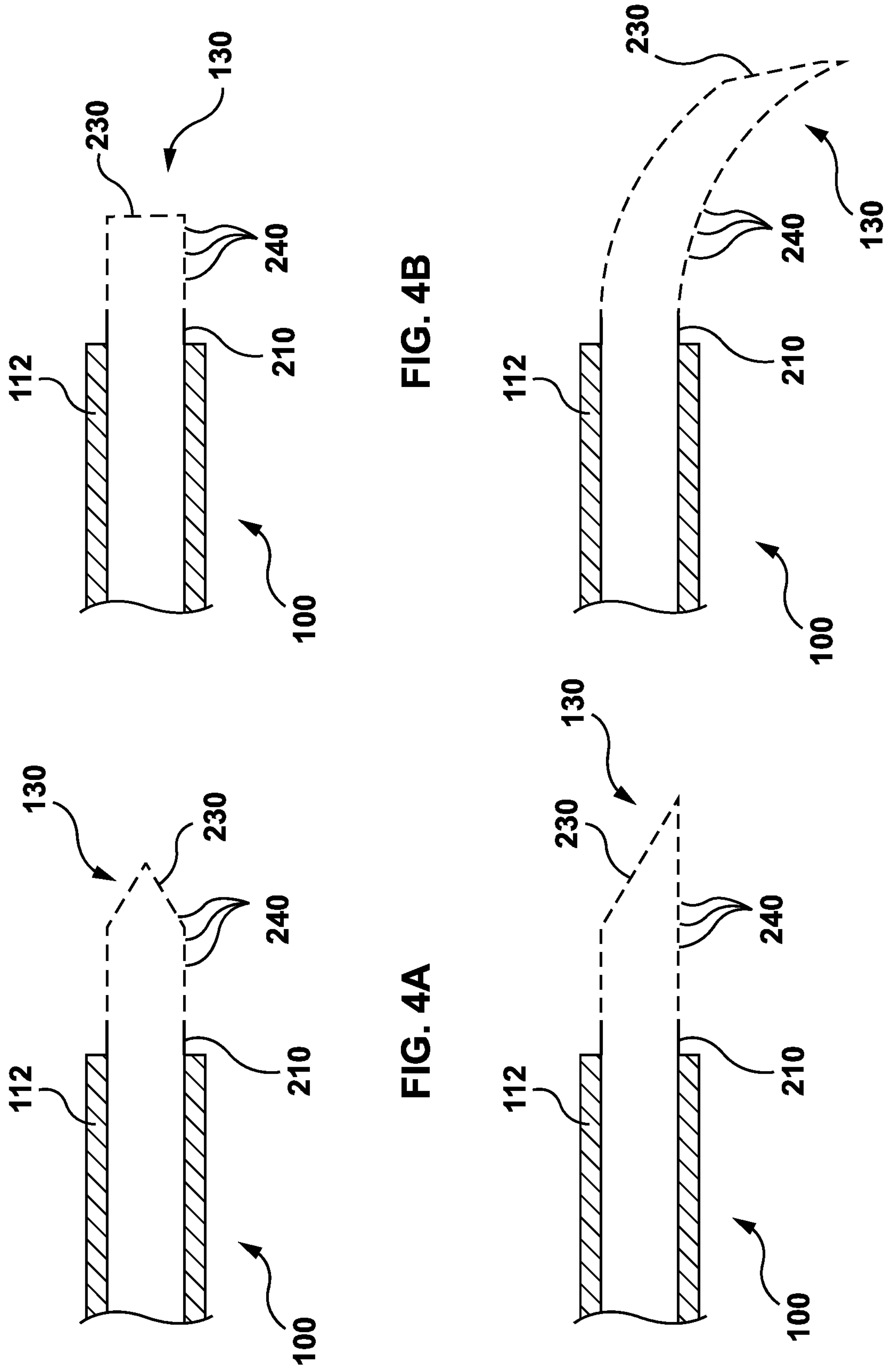
FIGS. 4*a*-4*d* illustrates various probe distal tip designs in accordance with an embodiment of the present invention.

With reference now to FIG. 3, the probe 100 is an elongated member comprising an elongate conductor 210, a distal region 220 with a distal tip 130, and a proximal region (not shown). As used herein, the term "distal" refers to the portion further away from the user, while the term "proximal" refers to the portion closer to the user, when the device is in use. As used herein, the term "irrigation flow rate" refers to the flow rate of the fluid as it is ejected from the probe, while the term "probe flow rate" references to the flow rate of the fluid contained within the probe. In some embodiments, the elongate conductor 210 comprises a layer of insulation 112, where the distal tip 130 of the probe 100 is exposed, forming an active portion or an active tip (e.g., an electrode 230). In some embodiments, the distal tip 130 comprises a domed tip, as depicted in FIG. 3. Alternatively, the distal tip 130 of the probe may be in the form of various geometries such as a sharp tip, flat tip, slanted sharp tip, or curve sharp tip, among others (as illustrated in FIGS. 4A-4D). In an alternative embodiment, the active portion or electrode 230 may be located at another location along the probe shaft 140. For example, the active portion or electrode 230 may be located in the distal region 220 rather than at the distal tip 130. High frequency energy such as radiofrequency (RF) energy is supplied from the generator (not shown) to the proximal region of the elongate conductor and travels along its length to an exposed region forming an electrode 230 at the distal tip 130 of the elongate conductor 210. Alternatively, a section along the elongate conductor 210 may be exposed. The electrode 230 delivers the RF energy to a targeted tissue. The distal tip 130 further comprises at least one or a plurality of orifices 240, such that a portion of the fluid circulating within the probe is ejected 250 from the distal tip 130 and a portion is recirculated 260. During the RFA procedure, a cooling fluid enters the lumen through the inlet tube 270, from an irrigation pump (not shown), and circulated through the probe 100. A portion of the cooling fluid is ejected from the orifices 240 and transferred to the tissue. The remaining fluid is recirculated, exiting the probe 100 via the probe lumen through the outlet tube 280, and flows back into the irrigation pump. In some embodiments, the remaining fluid may with withdrawn rather than re-circulated.

Figure 13:
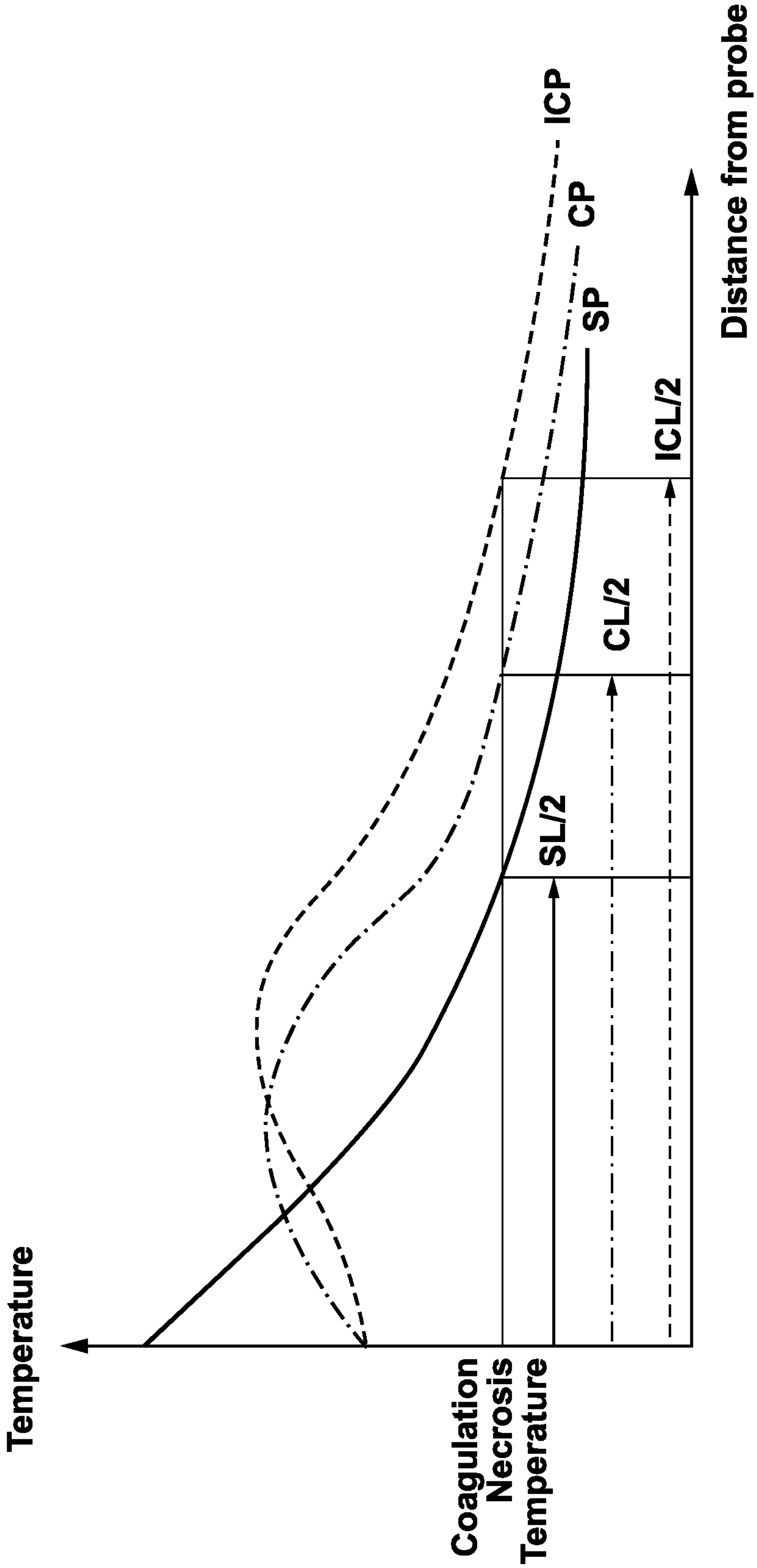
FIG. 13 illustrates the temperature profile created during lesion formation.

Circulating cooling fluid through the distal tip 130 of the probe 100 reduces the temperature of the surface of the distal tip 130, thereby reducing the temperature of the surrounding tissue. This allows the user to, effectively, increase the output of RF power while reducing the risks associated with the high temperature, allowing the energy output and/or RF application time to increase. By providing users with an irrigated cooled probe 100 in accordance with the present invention (that is, providing a probe with the ability to recirculate cooling fluid and the delivery of cooling fluid to the tissue), users can have a prolonged application of RF and/or allow the user to deliver higher amounts of RF power. In other words, the cooling of the tissue in close proximity to the probe 100 allows for a prolonged application of RF before the tissue proximate the probe 100 reaches a temperature at which cavitation and charring occurs (i.e., reduced risk of cavitation/charring given the same period of application at the same RF output). By enabling (with cooling) the longer application of RF and/or applying higher amounts of RF energy, the probe is capable of casting the temperature distribution at a distance from the probe resulting in lesions of increased size and distal projection. This is depicted in FIG. 13, which illustrates the temperature profile created by a standard probe SP (e.g., no cooling fluid re-circulated and/or ejected), a cooling probe CP (e.g., having cooling fluid re-circulated within the probe), and a probe of the present invention ICP (e.g., having cooling fluid re-circulated and ejected). The vertical axis indicates the temperature of the tissue. The dotted horizontal line labelled "Coagulation Necrosis Temperature" indicates the temperature at which the tissue cells either die or are injured. The horizontal axis indicates the distance from the probe. As shown, the lesion size increases when using a probe with cooling fluid being re-circulated and delivered to the tissue (SL is the lesion size formed by a standard probe, CL is the lesion size formed by a cooled probe, and ICL is the lesion size formed by a probe with re-circulating and ejecting fluid). While CP and ICP have substantially similar temperatures at the surface of the distal tip 130 of the probe 100, the infusion of fluid into the surrounding tissue results in the peak temperature being further away from the distal tip 130 of the probe 100. In other words, the infusion of fluid into the surrounding tissue results in larger lesions (as indicated by the ICP line in FIG. 13).

The ejection of fluid from the orifices 240 provides the tissue adjacent the probe with hydration. Hydrating the tissue reduces the risk of cavitation/charring. The drier the tissue is, the more it is prone to cavitation/charring. Increasing the temperature of tissue tends to dry the tissue. By hydrating the tissue as it is heated, the likelihood of cavitation/charring is reduced. Once the tissue undergoes cavitation/charring, the tissue does not transmit energy as efficiently (due to a decrease in thermal and/or electrical conductivity) which, ultimately, can result in undesirable lesion formation. The application of cooling fluid directly to the tissue, reduces the risk of cavitation/charring given the same period of application at the same RF output by increasing the moisture content. In addition to cooling the tissue, the application of fluid also increases thermal and electrical conductivity of the tissue.

Figure 14:
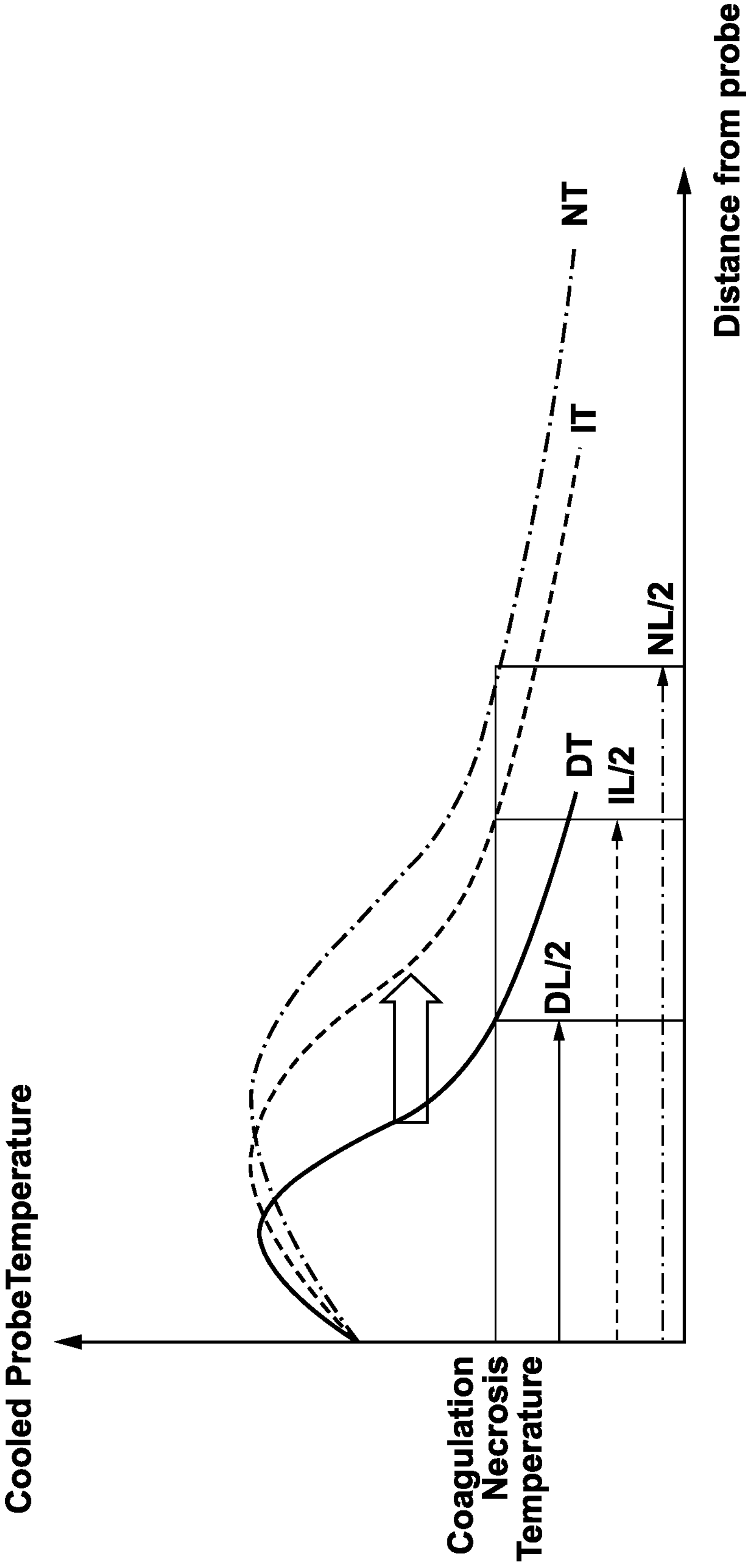
FIG. 14 illustrates the temperature profile created during lesion formation in desiccated tissue compared to normal tissue.

One example of the benefits of hydrating tissue can be observed when delivering energy to desiccated tissue. FIG. 14 illustrates the temperature profile of desiccated tissue when using a non-irrigated cooled probe (DT) and desiccated tissue when irrigation is provided (IT) and compares it to what the temperature profile of normal tissue (NT) would look like. The horizontal axis indicates the distance from the probe. As shown, the lesion size increases when hydrating the tissue (DL is the lesion size formed within desiccated tissue, IL is the lesion size formed when the tissue is hydrated with irrigation, and NL is the lesion size formed within normal tissue).

As described above, by increasing the thermal and electrical conductivity of the tissue, more RF energy may be applied before the tissue closest to the distal tip 130 reaches the target temperature. Prolonged and increased application of RF energy allows for an increase in lesion size and distal projection. By ejecting only a portion of the cooling fluid, while circulating the remaining, unresolved fluid ejection is avoided. Unresolved fluid ejection can lead to fluid pooling or fluid tracing in unknown or unexpected paths. The circulating fluid allows continued cooling of the probe while the flow rate can be adjusted to achieve a desired ejection volume.

The embodiment of FIG. 3 further comprises a temperature sensor. In an embodiment, the temperature sensor is as a thermocouple 290. The thermocouple 290 is within the distal region 220 of the probe 100. In a specific example, the thermocouple 290 comprises two wires 294, 296 disposed within the thermocouple lumen 292 which extends along the length of the elongate conductor 210. The two wires 294, 296 are insulated along their length. A distal tip of the two wires 294, 296 is not insulated resulting in a junction 298 being formed between the uninsulated portions of the wires. In an alternative embodiment, the thermocouple lumen 292 may comprise a hypotube and the thermocouple 290 may be formed using the hypotube and a single wire. The single wire may be insulated from the hypotube along the length of the elongate conductor 210 and a junction between the uninsulated portion of the wire and the hypotube is formed about the distal tip 130. In an embodiment, the thermocouple is continuous with (i.e., part of) the energy delivery pathway. In other words, the wires which form the thermocouple are part of the electrical circuit for the delivery of energy delivery to the probe. In embodiments where the thermocouple is part of the energy delivery pathway, the temperature reading may have noise from the energy delivery that can be filtered out prior to calculating temperature from the received signal.

In an alternative embodiment, the thermocouple 290 may be electrically and/or mechanically isolated from the energy delivery pathway. For example, the junction 298 of the thermocouple 290 may be electrically insulated from the thermocouple lumen 292 or the thermocouple lumen 292 may be comprised of a non-conductive material. In an alternative embodiment, the thermocouple 290 may be located outside of the probe 100, for example protruding from the distal tip 130, such that it is isolated from the energy delivery pathway. In these instances, the signal from the temperature sensor measurement is less likely to have noise from the energy delivery.

In yet another embodiment, the thermocouple 290 is not part of the energy delivery pathway and not electrically isolated from the energy delivery pathway. The thermocouple 290 comprises its own circuit for detecting signals, but may, during the operation of the device, come in electrical contact with the energy delivery circuit. In this embodiment, the electrical signal from the thermocouple 290 may comprise noise from the energy delivery which may need to be filtered out to calculate the temperature.

In all embodiments comprising a thermocouple 290, the thermocouple 290 provides a signal which allows for the calculation of the temperature at the thermocouple junction. Using the thermocouple 290, the generator detects and calculates the temperature which is used to adjust the amount of RF energy being delivered to the tissue.

In addition to determining the temperature of the surrounding tissue, the distal tip 130 of the probe 100 may be used to measure the impedance of the tissue. This may be achieved using the electrode 230 located at the distal tip 130. The measured impedance of the tissue may be detected by the generator which may be used to determine whether the amount of RF energy being delivered needs adjustment. For example, if there are high levels of fluid ejection, it may not be appropriate to rely on the temperature measurement to regulate RF energy delivery, as the thermocouple 290 may read the temperature of the cooling fluid rather than the target tissue. In these instances, the impedance of the tissue may be used as an indication of tissue desiccation and/or hydration. In one embodiment, the baseline impedance may be used to develop a relative measure of the progress of the ablation. In an alternative embodiment, an impedance profile may be achieved during ablation; this may be achieved through adjusting the cooling rate to create the impedance profile. For example, if the impedance of the tissue rises (i.e., indication of tissue desiccation), this may trigger tissue modulation by adjusting cooling rates or flow rates.

Figure 5A:
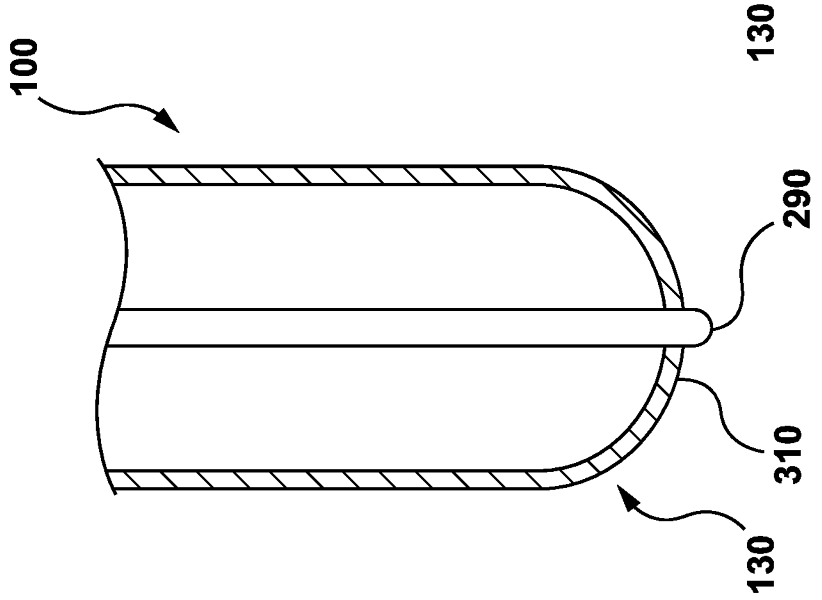
FIGS. 5*a*-5*c* illustrate the position of the temperature sensor in accordance with an embodiment of the present invention.
Figure 5B:
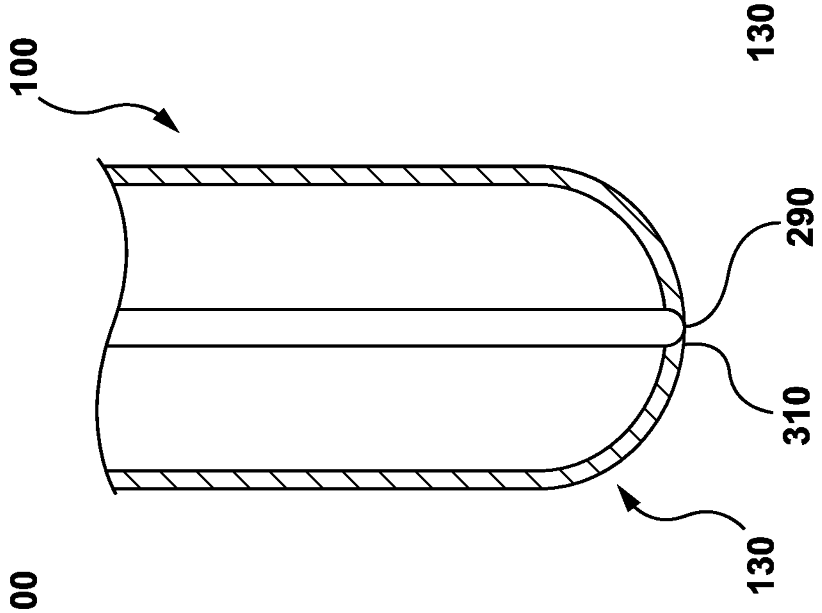
Figure 5C:
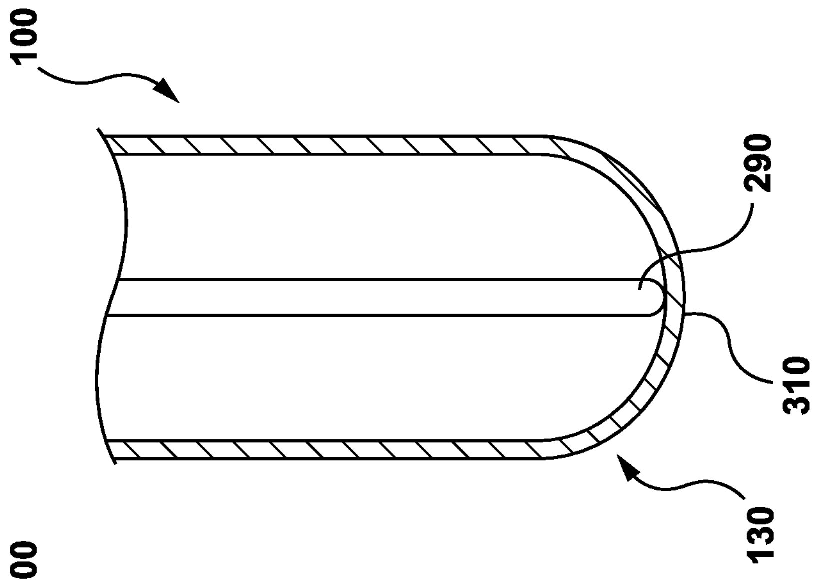

The thermocouple 290 may be positioned anywhere on the distal surface of the probe 100. FIG. 5A-5C illustrates some examples of how the thermocouple 290 may be positioned within the distal portion 130 of the probe 100. In one embodiment, the thermocouple 290 may be positioned such that it is exposed past the distal face 310 of the probe 100, as illustrated in FIG. 5A. In this embodiment, the protrusion of the thermocouple 290 may aid in isolating the thermocouple 290 from detecting the temperature of the cooling fluid (i.e., the reading of the thermocouple may be less influenced by the temperature of the cooling fluid). Alternatively, FIG. 5B illustrates the thermocouple 290 positioned flushed with the distal face 310 of the probe 100. In another embodiment, the thermocouple 290 may be positioned such that it is contained within the distal tip 130 of the probe 100, as illustrated in FIG. 5C. In alternative embodiments, the thermocouple 290 may be positioned away from the distal portion, for example on shaft of the elongate member.

In an embodiment of the present invention, the distal tip 130 of the probe 100 may further comprise a protrusion 132. The protrusion 132 may be formed such that it has a smaller diameter than the probe 100 (an example is shown in FIGS. 6A, 6C-6E). In alternative embodiments, the protrusion may be formed such that it has an equal diameter to the probe 100 (an example is shown in FIG. 6B). In some embodiments, the protrusion 132 may end in a sharp tip, slanted sharp tip, blunt tip, domed, or a curved sharp tip. In some embodiments, the orifices 240 may be located on the probe shaft 140, while in others the orifices 240 may be located on the protrusion 132. In an alternative embodiment, the orifices 240 may be located on the shaft 140 and the protrusion 132 (as depicted in FIG. 6E).

Figure 6A:
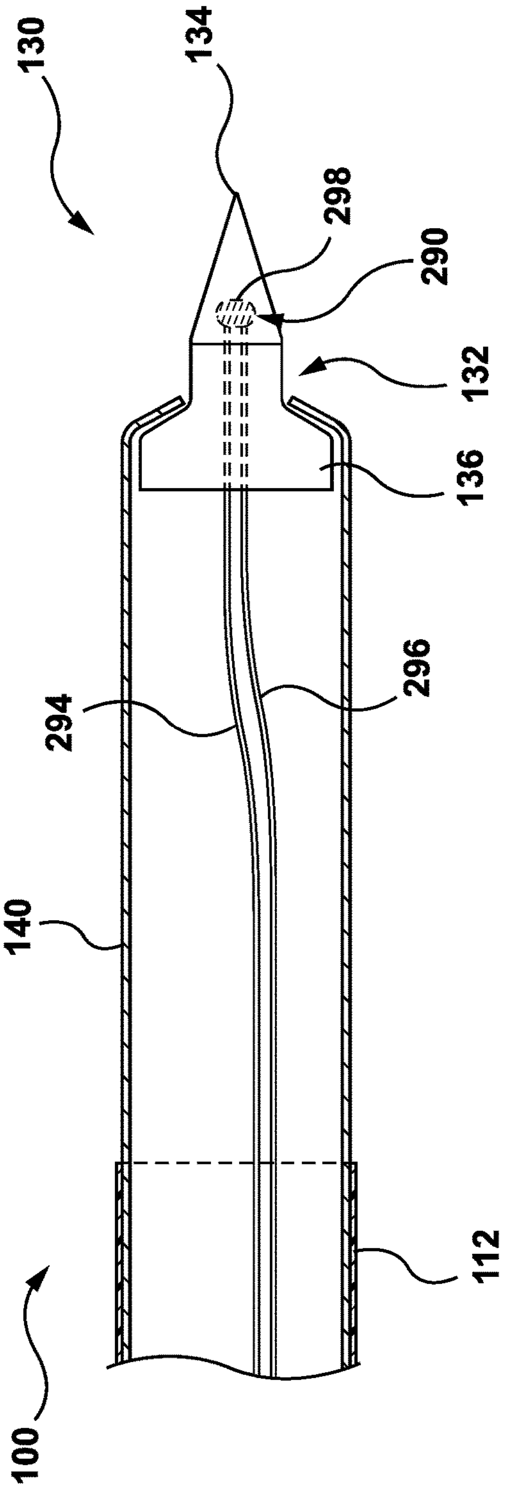
FIGS. 6*a*-6*e* illustrate various configurations for a protrusion at a distal tip of the probe in accordance with an embodiment of the present invention.
Figure 6B:
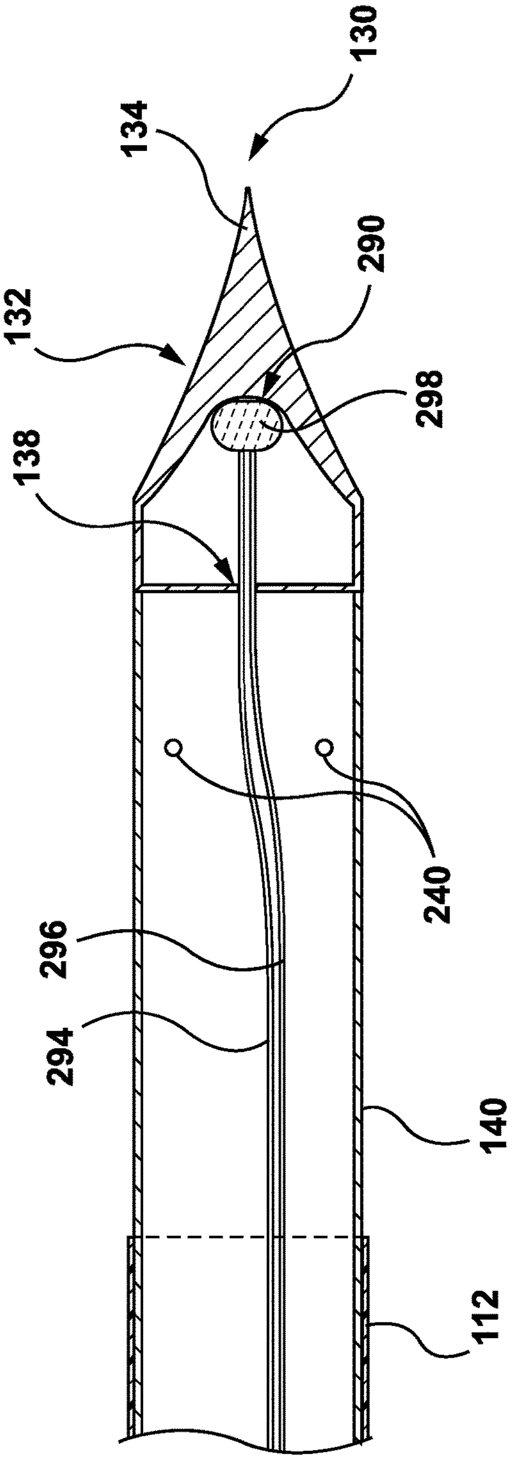
Figure 6C:
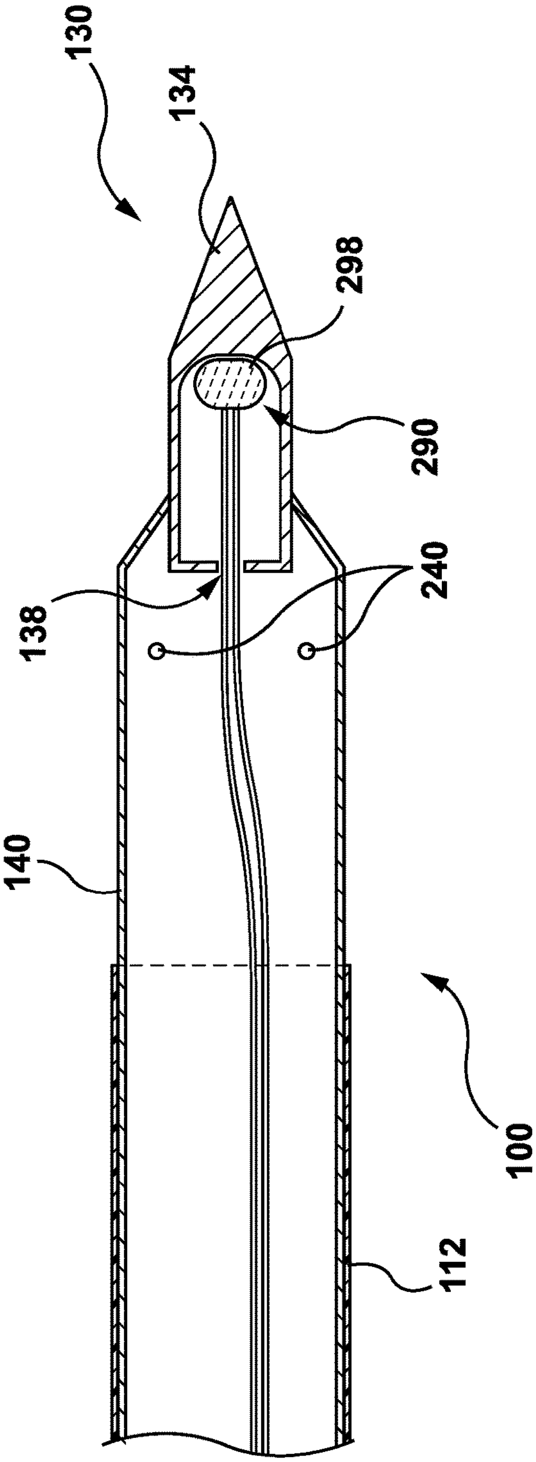
Figure 6D:
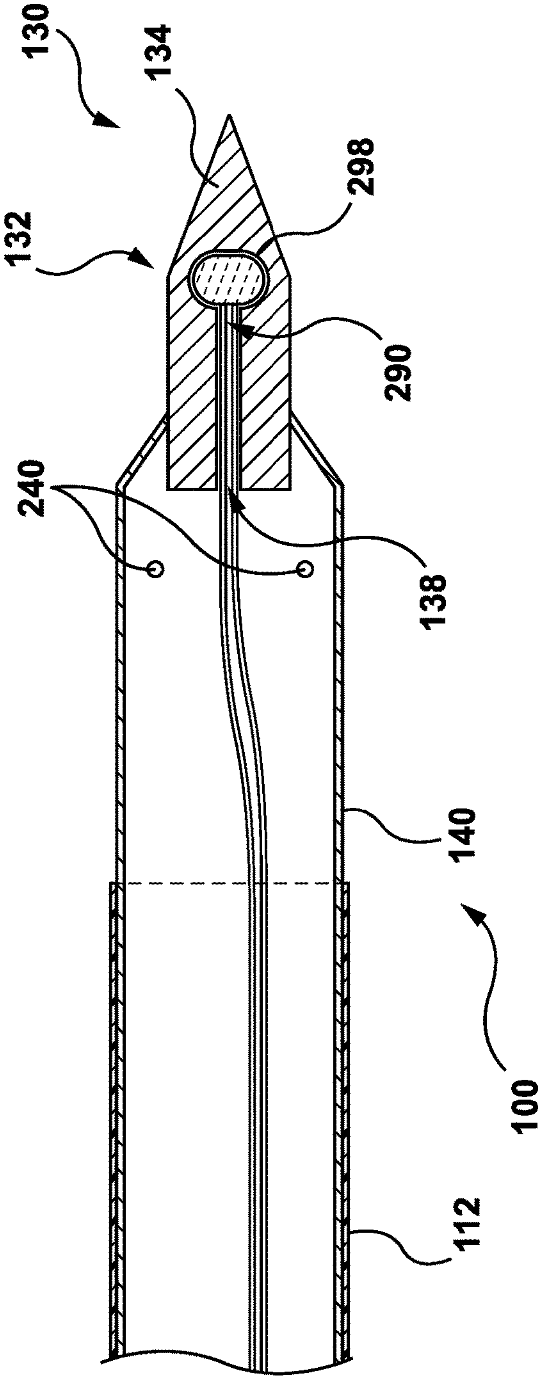
Figure 6E:
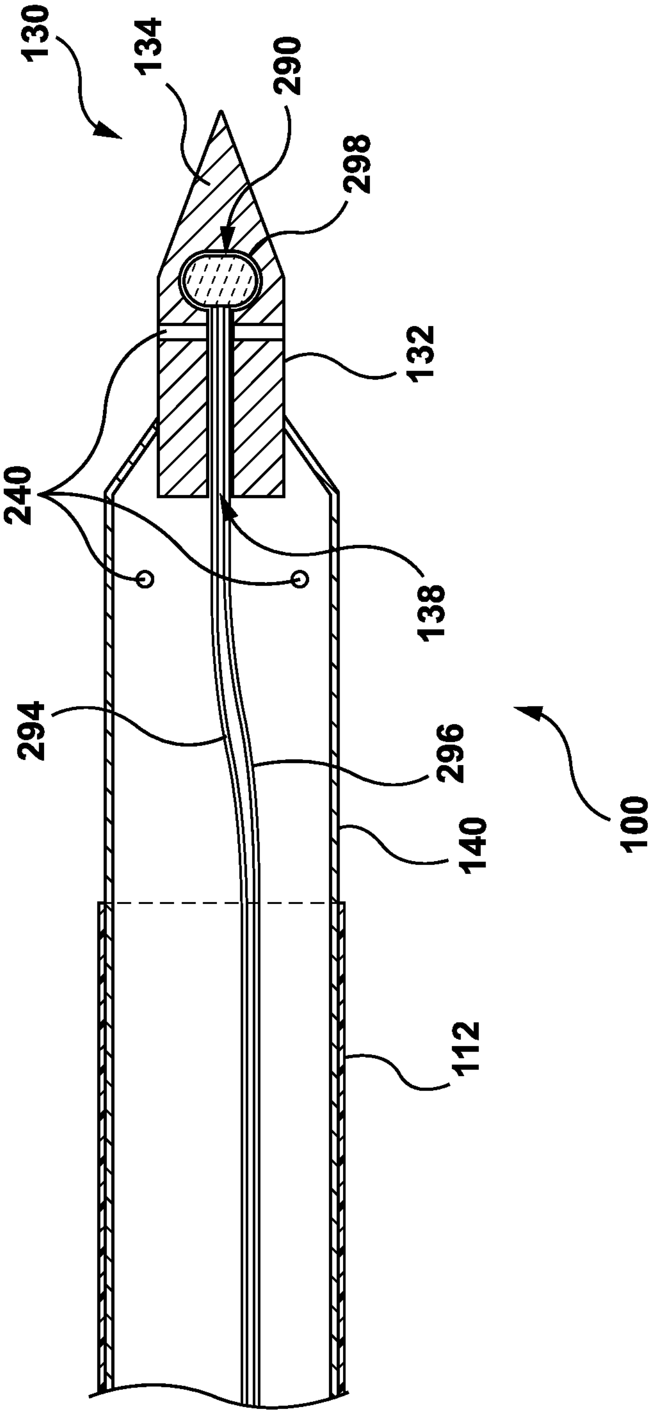

The protrusion 132 may be comprised, wholly, of a conductive material or, in an alternative embodiment, the protrusion 132 may be comprised of a combination of conductive 134 and non-conductive 136 material (an example of this is depicted in FIG. 6A). The non-conductive 136 portion may be positioned proximal to the conductive 134 portion. In such an embodiment, the non-conductive 136 portion may be attached (e.g., glued or locked/sealed mechanically) to the probe 100, while the conductive 134 portion may be attached (e.g., glued or locked/sealed mechanically) to the non-conductive 136 portion. In some embodiments, the conductive portion 134 may form part of (or all) the electrode 230.

In this embodiment of the present invention, the thermocouple 290 may be positioned within the protrusion 132, as depicted in FIGS. 6A-6E. In some embodiments, the thermocouple 290 may be welded inside the conductive 134 portion. The thermocouple 290 may be configured as previously described above. The protrusion 132 may comprise a hole 138, providing fluid communication between the shaft 140 and the protrusion 132. This allows for some of the irrigation fluid to reach the thermocouple 290. The hole 138 size may be tuned in order to tune the temperature response of the thermocouple 290. For example, in FIG. 6D, there is less surface area for contacting the thermocouple 290, thus, the thermocouple 290 is less effected by the internal cooling fluid. Having too much cooling fluid around the thermocouple 290 could result in unstable power delivery and, overall, an uncontrolled lesion formation.

Figure 7A:
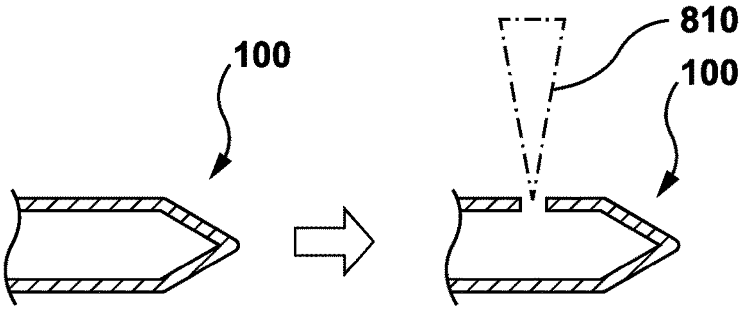
FIGS. 7*a*-7*d* illustrate various manufacturing methods to configure orifices on a probe in accordance with an embodiment of the present invention.
Figure 7B:
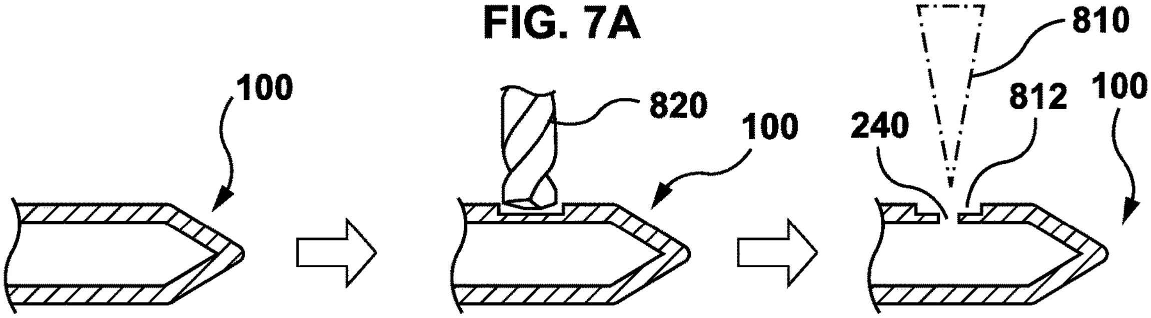
Figure 7C:
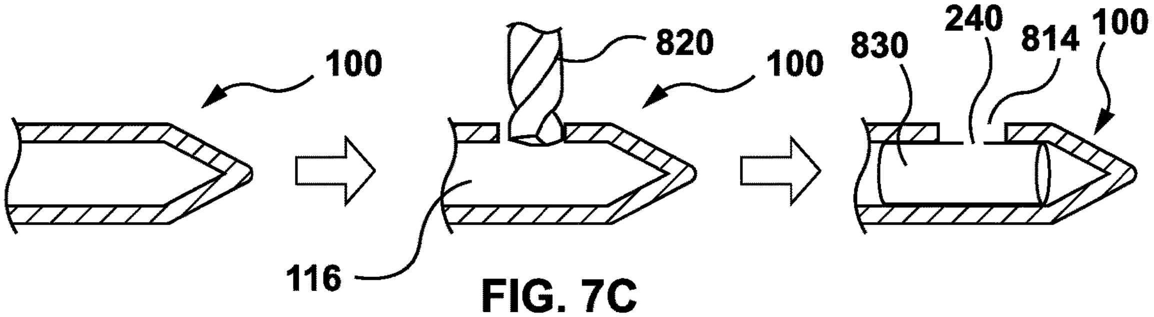

The distal tip 130 of the probe 100 comprises a plurality of orifices 240 which allows for the ejection of cooling fluid onto the tissue. FIGS. 7A-7D depict various methods of manufacturing to construct the plurality of orifices 240 at the distal tip 130 of the probe 100. In some embodiments, the orifices 240 may be manufactured into a thin tube by laser cutting the distal tip 130 (see FIG. 7A). During this process, a focused laser beam 810 melts or cuts the material. In another embodiment, the orifices 240 may be formed via drilling using a micro-drill. Alternatively, if using a thick tube, the orifices 240 may be formed using both a larger drill, to drill an initial cut, followed by a micro-drill to form the final, smaller, orifice 240. In yet another embodiment, a combination of drilling and laser cutting may be used to create a small orifice in a thick tube. An example of this is depicted in FIG. 7B, where a larger drill 820 may be used to form an initial cut 812 and a laser beam 810 may then be used to form the final, smaller, orifice 240. In another example, illustrated in FIG. 7C, a larger drill 820 may form a larger orifice 814 in the distal tip 130. A smaller tube 830, composed of a metallic or non-metallic material, may then be inserted through the lumen 116 of the probe 100. The smaller tube 830 comprises a smaller orifice 240 which will align with the larger orifice 814, forming the final, smaller, orifice 240. The smaller orifice 240 may be formed using either a micro-drill or a laser cut.

Figure 7D:
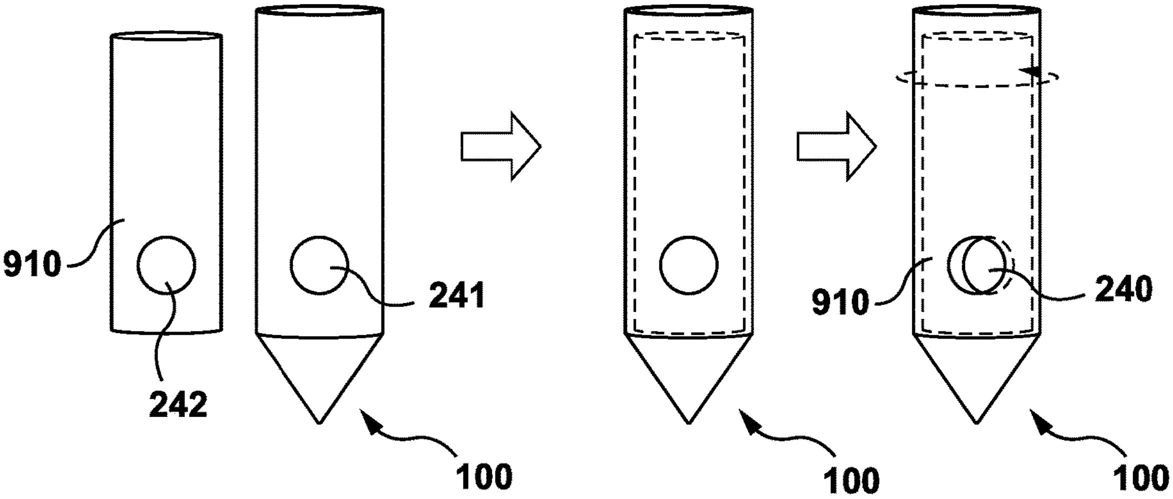

In an alternative embodiment, and with reference to FIG. 7D, the probe 100 may be formed with concentric tube 910 that is inserted into the lumen 116 of the probe 100. The distal end 130 of the probe 100 has an orifice 241 and the concentric tube 910 further comprises another orifice 242. The formation of each orifice 241 and 242 may be formed using drilling or laser cutting as described above. The concentric tube 910 can be rotated within the lumen 116 of the probe 100 such that the two orifices 241 and 242 overlap, forming the final, smaller, orifice 240. In a further alternative embodiment, the orifices 240 may be formed via mechanical puncturing.

Figure 8C:
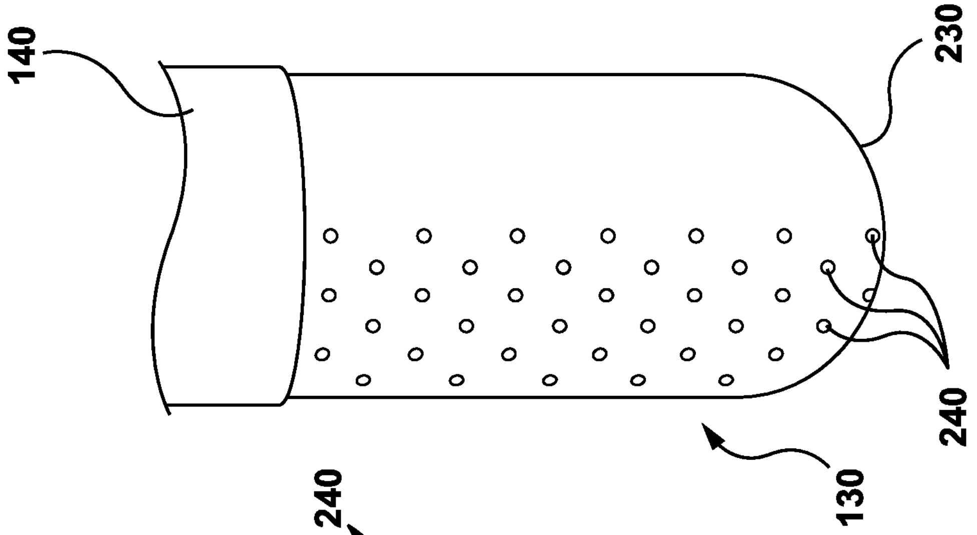
FIGS. 8a-8c illustrate the position of the probe's orifices in accordance with an embodiment of the present invention.
Figure 8B:
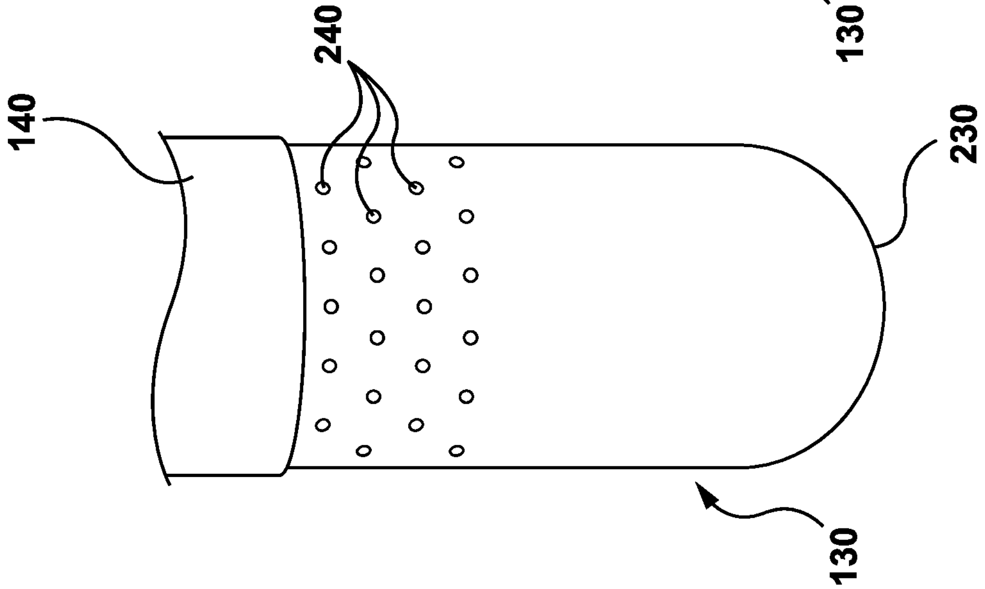
Figure 8A:
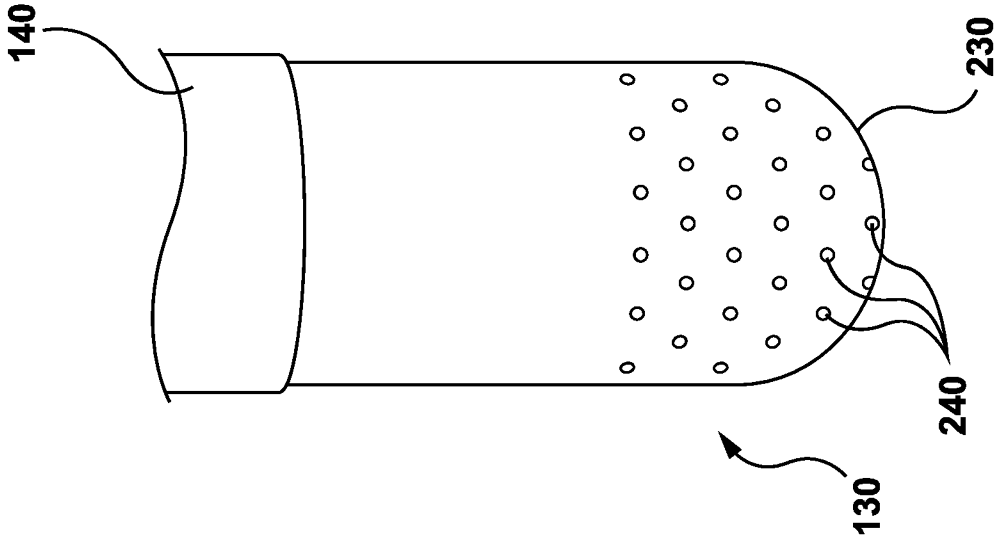

The orifices 240 may vary in positioning in order to provide targeted cooling to the tissue. For example, FIGS. 8A-8C illustrate a variety of placements of the plurality of orifices 240 for situations where the tissue around the probe 100 is heterogeneous; thus, rather than ejecting cooling fluid uniformly around the distal tip 130, cooling fluid may be delivered in one or more targeted areas. In general, cooling fluid should be targeted to the tissues which will undergo a rapid increase in temperature, as that signals that the tissue will dry out faster. FIG. 8A illustrates a distal tip 130 wherein the orifices 240 are concentrated distally on the distal tip 130. In this embodiment, the probe 100 may be positioned such that the target tissue for ablation is located at a proximal location of the distal tip 130 while the tissue located at a distal location of the distal tip 130 is more prone to cavitation/charring and, as such, requires cooling fluid to be applied. In a specific example, the probe 100 may be inserted such that the portion of the distal tip 130 comprising the orifices 240 is in contact with bone or dense tissue. Bone and dense tissue are more prone to faster increases in temperature, leading to the tissue drying out faster; the portion of the distal tip 130 located proximal the orifices 240 may be in contact with the tissue where ablation should occur in order to reach the target nerve. With the arrangement illustrated in FIG. 8A, the bone or dense tissue may receive cooling fluid while the target tissue will receive targeted ablation. Similarly, FIG. 8C illustrates a distal tip 130 of a probe 100 wherein the orifices 240 are concentrated on one side. In a specific example, the probe 100 may be inserted such that it is parallel to bone or dense tissue. Again, in this embodiment, the distal tip 130 may be configured such that the orifices 240 are positioned to eject cooling fluid at the bone or dense tissue, while the portion without the orifices 240 is positioned to ablate the target tissue. In an embodiment, the orifices are positioned such that cooling fluid is ejected away from the thermocouple to minimize the potential for the cooling fluid to interfere with temperature measurements by the thermocouple. For example, with reference now to FIG. 8B, the orifices 240 are located on the proximal portion of the distal tip; this embodiment may be used to prevent the ejected cooling fluid from interfering with the temperature reading of a thermocouple which is positioned at the distal tip 130. In this embodiment, the inlet and outlet tubes (not shown) may be positioned further (proximally) from the distal tip 130, reducing the amount of cooling fluid reaching the distal tip 130. However, with the orifices 240 being positioned in the proximal portion, cooling fluid is still allowed to be ejected from the probe 100.

In some embodiments, the diameters of the orifices 240 may vary over the surface of the electrode 230. The diameter of the orifices 240 may range from 0.2 μm to 0.2 mm. Varying the orifices' 240 diameters allow for compensation for varying inlet pressures at each hole, preferential fluid ejection (such as ejecting more fluid in a specific area) and may enable selective delivery of fluid. Specifically, orifices 240 with smaller diameters require high pressure to initiate fluid delivery compared to orifices 240 with larger diameters; thus, the user or system may be able to control which orifices 240 are ejecting fluid by altering the fluid pressure.

Figure 9A:
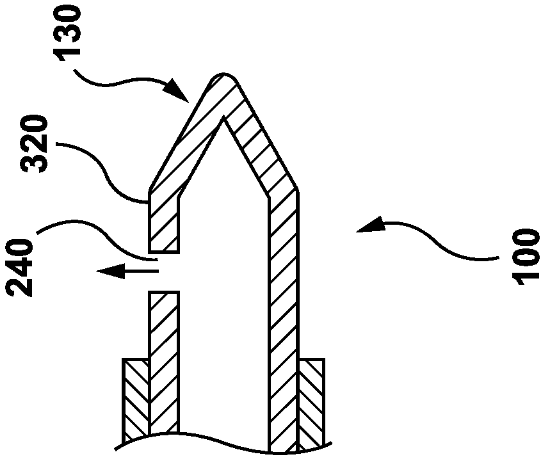
FIGS. 9a-9c illustrate various configurations to provide orifices with directionality in accordance with an embodiment of the present invention.
Figure 9B:
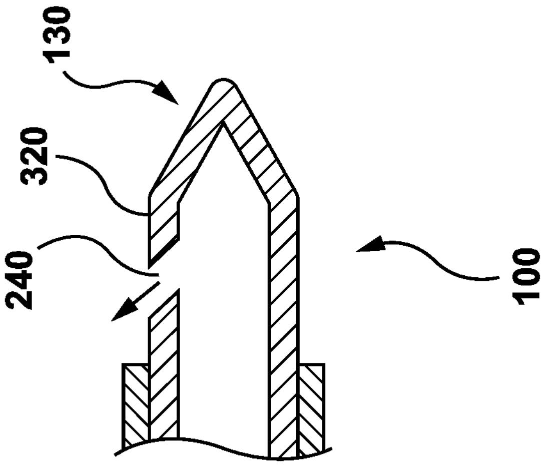
Figure 9C:
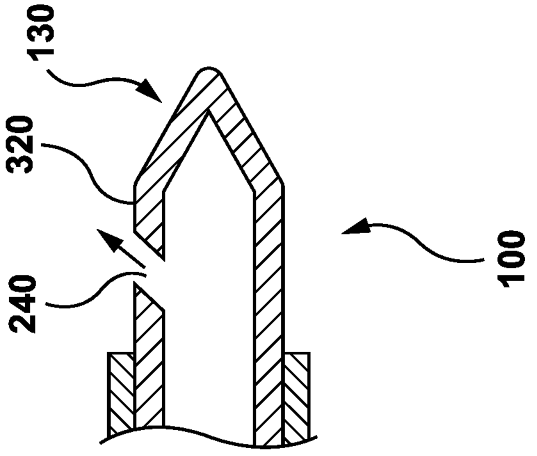

In some embodiments, the orifices 240 may be formed in a way that the irrigation is ejected from the system in a specific direction. For example, the orifice 240 may be configured with a taper that would guide the fluid ejection in a specified orientation. In other words, an orifice 240 may be tapered in one direction to direct the fluid ejection. The taper of the orifice 240 may be created by manufacturing the orifice 240 on an angle or by removing further material surrounding the orifice 240 to create directionality. By providing orifices 240 with directionality, most of the irrigation fluid may be ejected towards hot spots around the probe 100, thereby mitigating temperature spikes around the tissue; this, ultimately, may aid in preventing tissue charring. In addition, providing orifices 240 with an orientation may allow for higher delivery of power if the orientation of the orifices 240 is directed towards the temperature sensing element (e.g., thermocouple). This would allow for the formation of larger lesions at the target tissue. Some examples of orientation can be seen in FIGS. 9A-9C. FIG. 9A illustrates an orifice 240 with an orientation perpendicular to the probe 100 surface 320. FIG. 9B depicts an orifice 240 with an orientation where the irrigation fluid is ejected in the proximal direction. FIG. 9C depicts an orifice 240 where the irrigation fluid is ejected in the distal direction. It would be understood by the person skilled in the art that the orifice 240 may be tapered or configured to eject fluid in any direction. In some embodiments, the probe 100 may comprise orifices 240 with one or a combination of orientations.

Figure 10B:
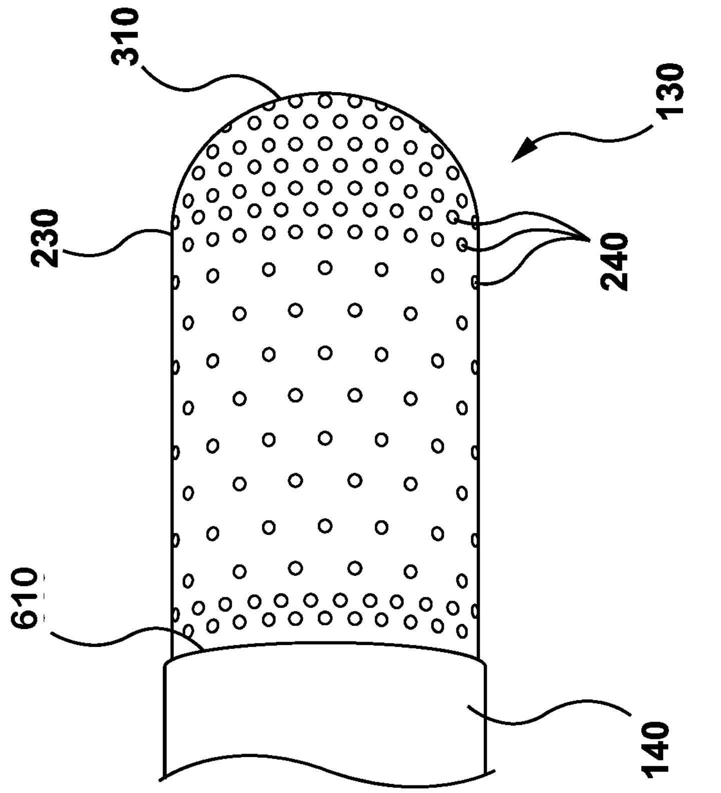
FIGS. 10a-10b illustrate the dispersion of the probe's orifices in accordance with an embodiment of the present invention.
Figure 10A:
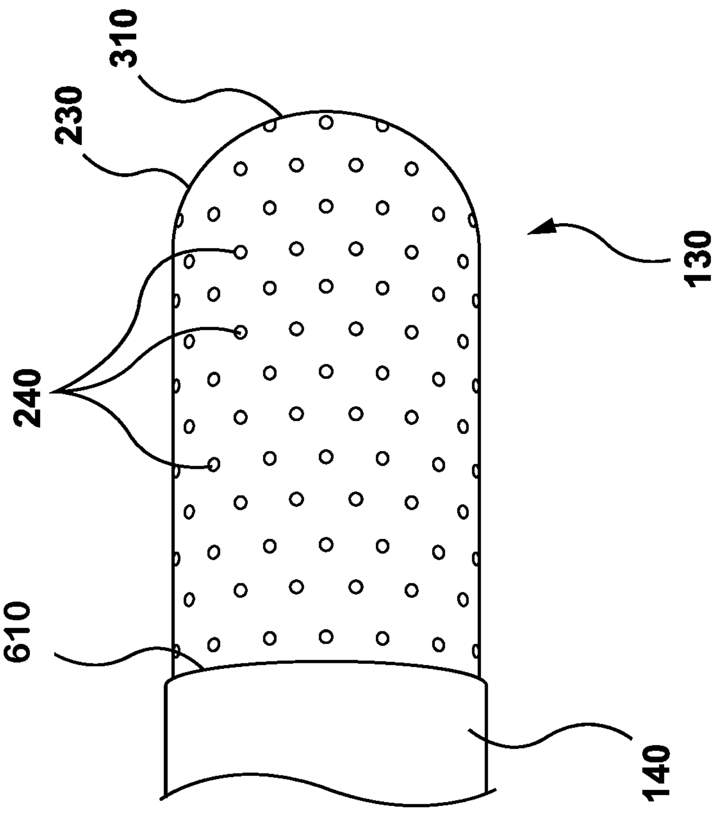

The plurality of orifices 240 may be used to address current density which occurs on the electrode 230. The current, as it flows from the generator to the electrode 230, does not form a uniform profile on the electrode 230. Rather, at the interface 610 and the distal face 310 of the electrode 230 the current density is relatively greater (denser) than the distal face away from interface 610. In these areas of increased current density, the surrounding tissue will heat (and dry out) faster than areas where the current is not as dense. FIGS. 10A-10B illustrate various configurations of the distal tip 130. FIG. 10A illustrates a distal tip 130 where the orifices 240 are uniformly distributed. In another embodiment, the orifices 240 may be concentrated or non-uniformly distributed in one portion of the distal tip 130 (FIG. 10B). The orifices 240 may be positioned such that there is a higher concentration of orifices 240 in areas where there is more current density to increase the amount of cooling fluid to areas of tissues which may be exposed to denser current and thus higher temperatures. Alternatively, the orifices 240 may vary in size (e.g., diameter). The varying sizes may be configured to address areas of higher current density on the distal tip 130.

It should be appreciated that the positioning, sizing, orientation, and concentration of orifices 240 may be combined with one another to achieve the desired cooling fluid ejection profile of the distal tip 130.

Figure 11:
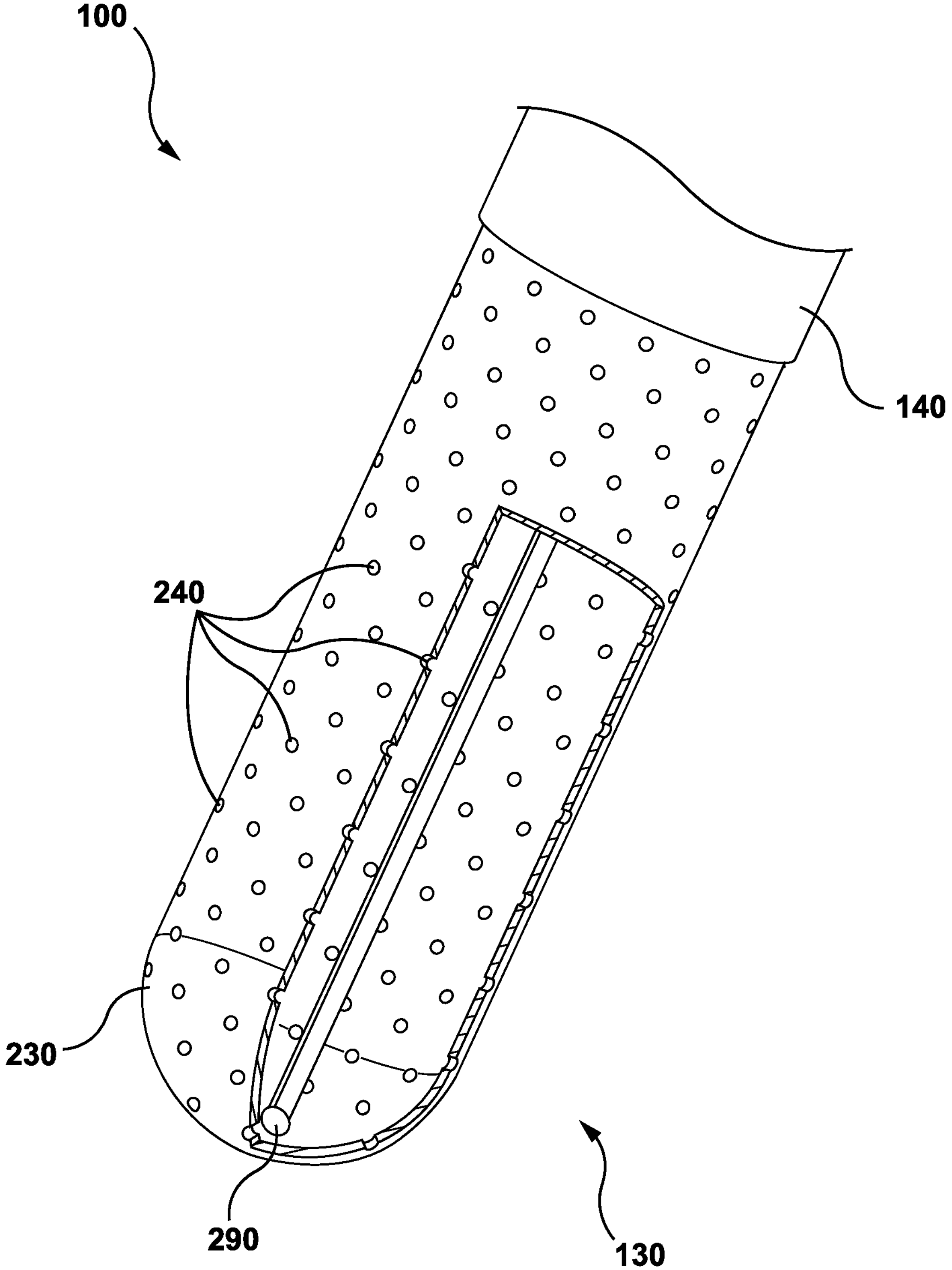
FIG. 11 illustrates a cut-away view of an ablation probe in accordance with an embodiment of the present invention.

FIG. 11 illustrates the distal tip 130 of a probe 100 comprising a plurality of orifices 240 positioned around the distal tip 130. A cut-away portion of illustrates an exemplary position of the thermocouple 290 positioned distally. In this embodiment, the thermocouple 290 is positioned at a distal end of the probe 100, and the orifices 240 are uniformly distributed across the surface of the distal tip 130.

Figure 12:
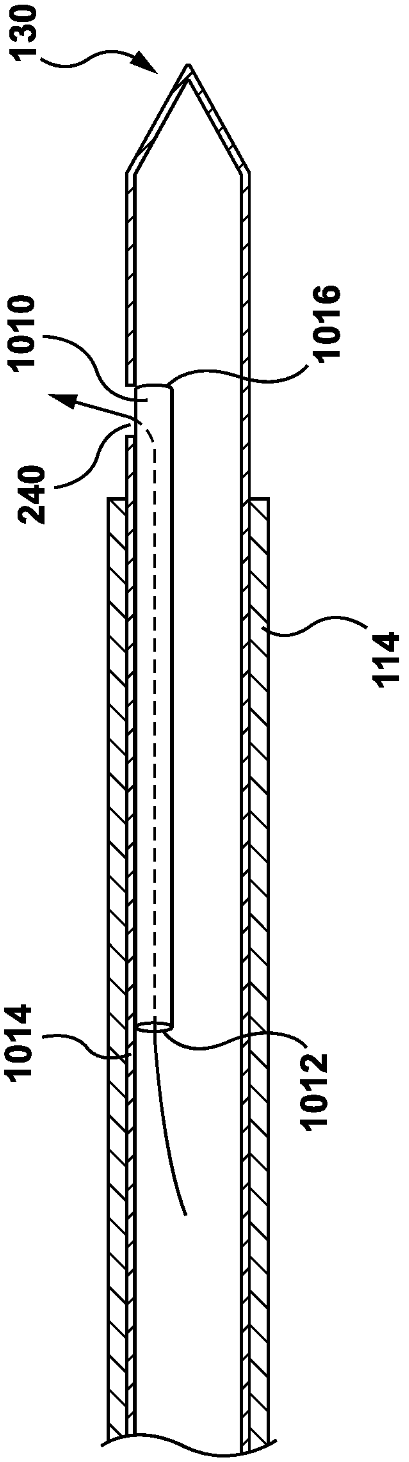
FIG. 12 illustrates a probe with a pneumatic resistor in accordance with an embodiment of the present invention.

In some embodiments, it may be desirable to have larger orifices 240 at the distal tip 130 to avoid various issues associated with smaller holes (e.g., technical challenges associated with manufacturing limitations). With reference to FIG. 12, in some embodiments, the probe 100 may further comprise at least one pneumatic resistor. The pneumatic resistor reduces the internal pressure of fluid, allowing the distal tip 130 of the probe 100 to comprise larger orifices 240 while maintaining a lower irrigation flow rate. In some embodiments, the pneumatic resistor may be configured as a small tube 1010 positioned along the irrigation flow path, proximate to the orifice 240. The irrigation fluid would flow into the tube 1010, along the length of the tube 1010, and exits out of the orifice 240 (see flow path 1012 in FIG. 12). In some embodiments, the tube 1010 may be coupled to the inner surface 1014 of the probe 100 through gluing or laser welding. The length, diameter/surface area, and inner surface finish of the tube 1010 defines the resistance provided by the pneumatic resistor and, the resistance defines the irrigation flow rate. The tube 1010 may be configured to have any geometric shaped cross section, including but not limited to, a circular, square, or rectangular cross section. Further, in some embodiments, the cross section of the tube 1010 may vary along its length. For example, the cross section may taper (e.g., from a larger diameter to smaller diameter or smaller diameter or larger diameter). Additionally, in some embodiments, the tube 1010 may be shaped such that it is linear (straight), curved, or a combination of the two.

In some embodiments, the probe 100 with the pneumatic resistor may further comprise a thermocouple 290. The thermocouple 290 may be positioned as previously described above. Alternatively, the thermocouple 290 may be placed along the resistor (e.g., tube 1010). As an example, the thermocouple 290 may be placed at the distal end 1016 of the resistor. In an alternative embodiment, the pneumatic resistor may form part of the thermocouple 290. In other words, the thermocouple 290 may comprise the tube 1010 and a single wire. As an example, the single wire may be insulated from the tube 1010. The thermocouple 290 is formed at a junction between an uninsulated portion of the wire and the tube 1010.

A method of lesioning a target site (e.g., nerve tissue) with the probe 100 of the present invention involves the steps of: (a) inserting the probe 100 into a patient; (b) positioning the distal tip 130 of the probe 100 at a target location/tissue; (c) delivering energy (e.g., radiofrequency energy) to the target tissue; (d) delivering a portion of cooling fluid to the tissue while having a portion of the cooling fluid recirculated through the probe; and, (e) forming a lesion at the target location/tissue.

In some embodiments of the present invention, step (a) involves inserting an introducer assembly comprising a cannula towards the target location. In some instances, the cannula may further comprise a stylet, disposed therein. In some embodiments, the target location may be a soft tissue, such as the medial branches of the dorsal ramus in the lumbar spine. In alternative embodiments, a harder tissue, such as a vertebral body, may be the target location. The introducer assembly may be inserted into the soft tissue. Upon insertion of the introducer assembly, various visualization techniques may be used to confirm positioning (e.g., ultrasound or fluoroscopy). Once the introducer assembly is positioned at the target location, the stylet (if being used) is withdrawn. The probe 100, of the present invention, is then inserted through the cannula and advanced towards the target location. Various visualization techniques may be used to confirm target location (e.g., fluoroscopy, ultrasound, etc.). In some embodiments, a grounding pad is placed on the skin of the patient. The grounding pad acts as a return electrode, completing the circuit during the delivery of energy. In another embodiment, at least one additional probe 100 may be inserted, acting as the return electrode wherein a lesion is formed between the probes (as described previously). The probes may be monopolar and/or coaxial, bipolar, probes. RF energy may be supplied using an RF generator, connected at the proximal end of the probe 100. As RF is delivered to the target location, a lesion is formed adjacent the electrode 230. In some embodiments, power delivery can range between 0-50W and may be delivered in the range of 0.5-10 minutes. Cooling fluid may be delivered to the target tissue via a cooling pump connected at the proximal end. The cooling fluid enters the probe 100 via an inlet tube. As previously described, a portion of the fluid is ejected from the distal tip 130 of the probe 100 while the remainder is re-circulated back to the cooling bump via an outlet tube. In an alternative embodiment, the remainder of fluid is withdrawn rather than re-circulated. The selected coolant temperature into the system may range from a minimum temperature of −7° C. to a maximum temperature of 100° C. In some embodiments, the selected coolant temperature into the system may range from just above 0° C. to up to 30° C. In some embodiments, the minimum temperature is determined by the freezing point of the chosen coolant. In a specific example, if a saline with higher-than-normal saline (e.g., 20% higher) than the minimum temperature may be around −17° C. The maximum temperature is determined by the boiling point of the chosen coolant.

In some embodiments, the delivery of cooling fluid may occur prior to ablation, further described below. Additionally, the probe flow rate and/or irrigation flow rate may be controlled throughout the procedure via a feedback mechanism, as described below.

In some embodiments, the energy delivery is controlled based on an energy delivery parameter. The energy delivery parameter may be a thermal and/or electrical characteristic of the tissue. In some embodiments, the energy delivery parameter is monitored through the lesioning procedure. The energy delivery is adjusted based on comparing the measured energy delivery parameter of the tissue to a predetermined energy delivery parameter (e.g. the generator is adjusted/modulated). In another embodiment, the probe flow rate is controlled based on an energy delivery parameter and thereby controlling the irrigation flow rate (e.g. the cooling pump is adjusted/modulated). During the procedure, the measured energy delivery parameter of the tissue is compared to a predetermined energy delivery parameter and the probe flow rate is adjusted accordingly. In a further embodiment, the energy delivery and the probe flow rate are controlled based on the energy delivery parameter. In other words, a thermal and/or electrical characteristics of the tissue measured during the lesioning procedure controls the energy delivery and the probe and irrigation flow rates. In some embodiments, the energy delivery parameter is the temperature of the tissue. In another embodiment, the energy delivery parameter is the impedance of the tissue. In another embodiment, the energy delivery parameter is a combination of thermal and/or electrical characteristics of the tissue.

In some embodiments, the temperature of the tissue is detected (measured) via a temperature sensor (e.g., a thermocouple 290). The generator may adjust/modulate the delivery of energy based on the temperature of the tissue. The cooling pump may adjust/modulate the delivery of cooling fluid based on the temperature of tissue.

In some embodiments, the impedance of the tissue may be detected (measured) by the probe 100. The generator may adjust/modulate the delivery of energy based on the impedance of the tissue. The cooling pump may adjust/modulate the delivery of cooling fluid based on the impedance of the tissue.

Pre-Ablation Preparation

In accordance with an embodiment of the invention, the target tissue is primed prior to ablation. In other words, the electrical and/or thermal characteristics are modulated or altered prior to ablation to improve the tissue's susceptibility to ablation. Priming optimizes the tissue properties prior to the RFA to improve consistency and volume of tissue ablation. The electrical and/or thermal characteristics may be used as energy delivery parameters. The electrical and/or thermal characteristics are measured by stimulating the tissue and measuring the response of the tissue. In other words, the stimulus evokes a measurable response in the tissue providing a biomarker for the tissue type. In some embodiments the stimulus is RF energy. The RF energy may be delivered across a known period of time. Alternatively, the RF energy is delivered until the tissue reaches a predetermined temperature. In other embodiments the stimulus is cooled irrigation. In some embodiments, the stimulus is cooling via an internally cooled probe. Similarly to the RF energy, the irrigated and/or internal cooling may be delivered across a known period of time or delivered until the tissue reaches a predetermined temperature. Furthermore, in some embodiments, the stimulus is a combination of RF energy, internal cooling and/or cooled irrigation. In some embodiments, the measured response is the temperature change of the tissue, effective heat capacitance, thermal diffusivity, thermal conductivity, electrical conductivity and/or impedance.

Figure 15:
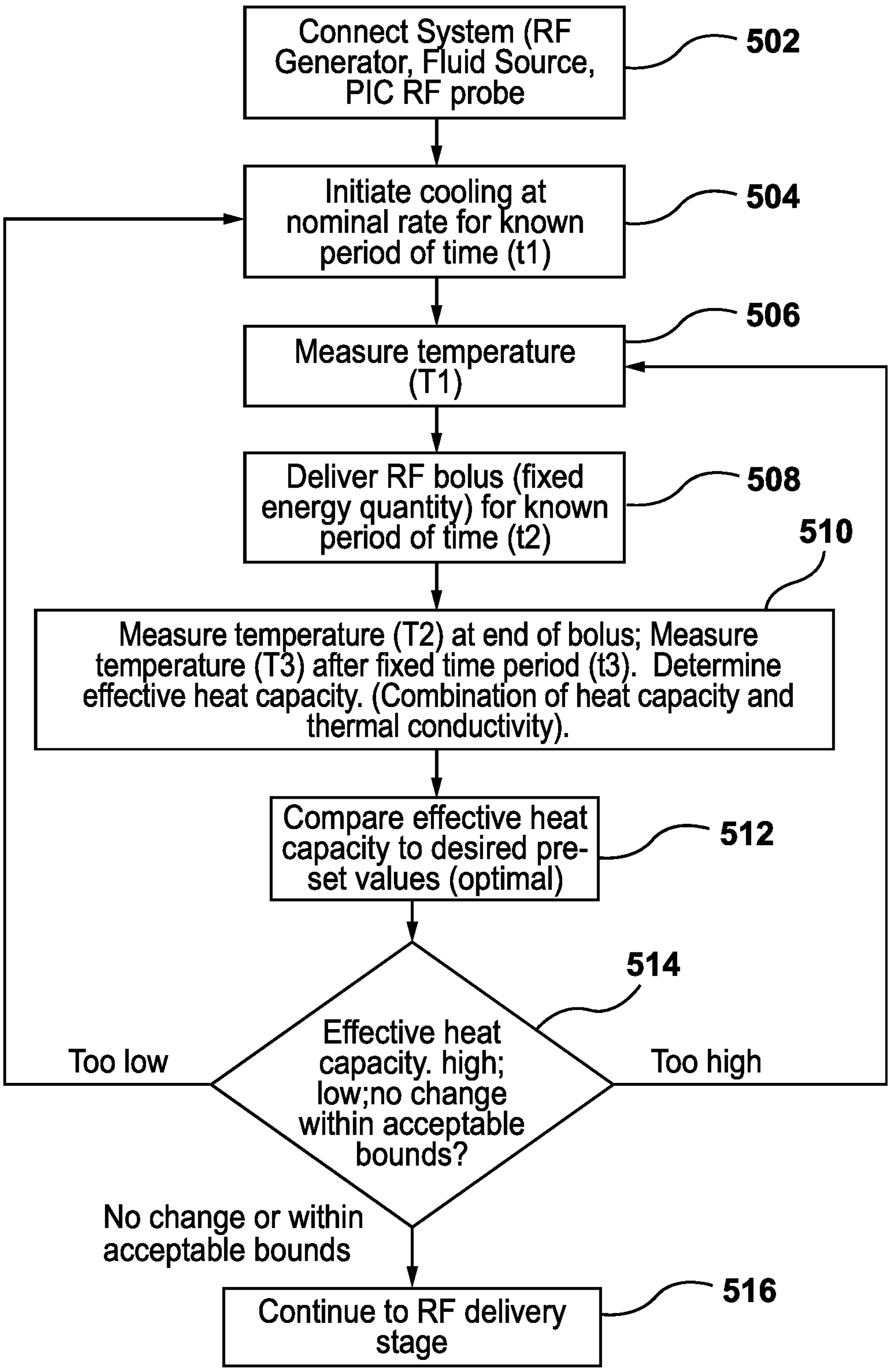
FIG. 15 is a flow chart showing a method in accordance with an embodiment of the present invention.

FIG. 15 is a flow chart illustrating an example of a method of priming the tissue. In this embodiment, the stimulus is RF energy and the measured thermal and/or electrical characteristic of the tissue is effective heat capacitance. It would be known to those skilled in the art that other stimuli such as cooling or irrigation could be used, and other thermal and/or electrical characteristics such as impendence, temperature change of the tissue, thermal diffusivity, and/or thermal conductivity could be measured. At step 502, an energy delivery device such as the probe 100 is connected to an RF generator and a fluid source. The probe is positioned against the target tissue. At step 504, the probe is cooled at a nominal or standardized rate for a known period of time. The standardized rate may be selected based on the tissue. In one example, a probe flow rate of in the range of 0-50 mL/min is used for bone. In another example, a higher flow rate is used for tissues with high levels of vascularity such as liver tissue. As the probe 100 is cooled, the cooling fluid is ejected from the orifices at the distal tip of the probe. The target tissue is irrigated by the fluid exiting the probe. The irrigation hydrates the tissue prior to delivering ablation. The thermal and electrical characteristics of the tissue are modulated or altered due to the irrigation and hydration of the tissue. At step 506 a first temperature, T1, of the target tissue is measured. In step 508, a stimulus such as an RF bolus is delivered to the target tissue. The RF bolus is a predetermined energy quantity. An RF bolus is a non-therapeutic or non-ablative amount of RF energy. The RF bolus is an energy deposition that is used to develop a biomarker for the tissue type. In one embodiment, the RF bolus is delivered for a predetermined amount of time, thereby increasing the temperature of the tissue to non-destructive levels (I.e., non-ablative) in order to measure the tissue properties in terms of their response to cooling and irrigation. In an alternate embodiment, the RF bolus is delivered until the tissue reaches a predetermined temperature while measuring the time to determine the response of the RF stimulus. After the delivery of the RF bolus, a second temperature, T2, is measured as shown in step 510. A thermal and/or electrical characteristic of the tissue is determined by measuring the response to the stimulus. For example, the effective heat capacity is determined by the amount of energy supplied divided by the corresponding change in temperature. The effective heat capacity is a combination of the heat capacity and the thermal conductivity. In some embodiments, step 510 further comprises the step of measuring a third temperature, T3, of the target tissue. Temperature T3 is measured a predetermined period of time after the RF bolus has been delivered in order to determine the thermal conductivity of the tissue.

Figure 16:
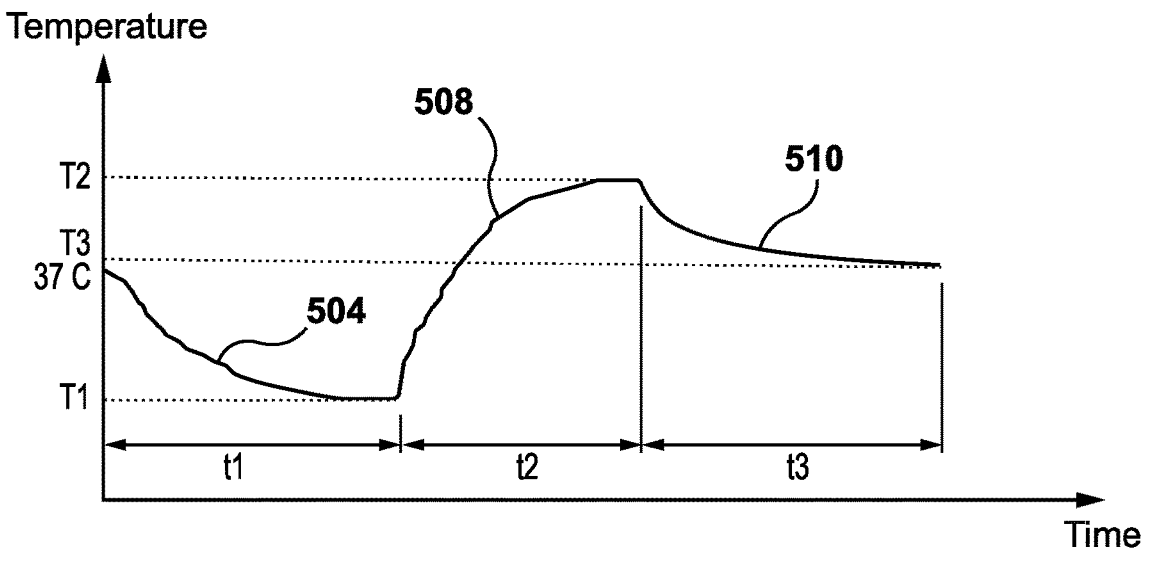
FIG. 16 illustrates a temperature graph in accordance with an embodiment of the present invention.

FIG. 16 shows an example of the temperature measurements for the workflow of FIG. 15. The tissue starts at body temperature. The tissue is cooled and irrigated until the time reaches t1 and the tissue temperature T1 is measured. An RF bolus is emitted across t2. After the RF bolus is administered, the temperature T2 is measured. In some embodiments, temperature T3 is measured after time t3.

At step 512, once the effective heat capacity of the tissue is determined, it is compared to desired pre-set or predetermined values. In an embodiment, the desired pre-set or predetermined value is the optimal heat capacity value for ablating tissue. If the effective heat capacity is lower than the desired pre-set values 514, the process is brought back to the cooling at step 504. The tissue is further cooled and irrigated and the effective heat capacity is determined again (Steps 506-510). Once again, the determined effective heat capacity of the tissue is compared to the desired pre-set values. If the effective heat capacity of the tissue is higher than the desired pre-set values 514, the process is brought back to step 506. The effective heat capacity of the tissue is determined again (Steps 506-510) without additional cooling or irrigation. When the effective heat capacity is within the acceptable bounds of the desired pre-set value 514, the process continues to the step of RF delivery 516. In other words, the steps of cooling (if heat capacity too low) or waiting, ablating and/or withdrawing fluids (if heat capacity too high) continues until the effective heat capacity is within acceptable predetermined bounds. Once the effective heat capacity is within acceptable bounds, RF is delivered (step 516). In some circumstances, the effective heat capacity of the tissue is incapable of being increased or decreased to within the acceptable bounds of the pre-set value. In such circumstances, after several cycles between steps 504-510 or step 506-510 have taken place, the effective heat capacity will no longer change in a material way despite additional cycles of said steps. Accordingly, at step 514, if the effective heat capacity value of the tissue has not been determined to be within the acceptable bounds after a predetermined number of cycles of steps 504-510 or steps 506-510 above, then RF is delivered at step 516. In an alternative embodiment, instead of waiting a predetermined number of steps before proceeding to RF delivery (step 520), the system repeats the cycle for a predetermined amount of time.

In some embodiments, the fluid flow rate and RF energy delivered by the probe of step 516 are influenced by the effective heat capacity data determined in the priming process. For example, in tissues with a relatively high effective heat capacity, a greater amount of energy is delivered to create the desire ablation pattern. In tissues with a relatively low effective heat capacity, the fluid flow rate of the cooling fluid circulating through the probe may be increased to reduce the chance of charring the target tissue.

Figure 17:
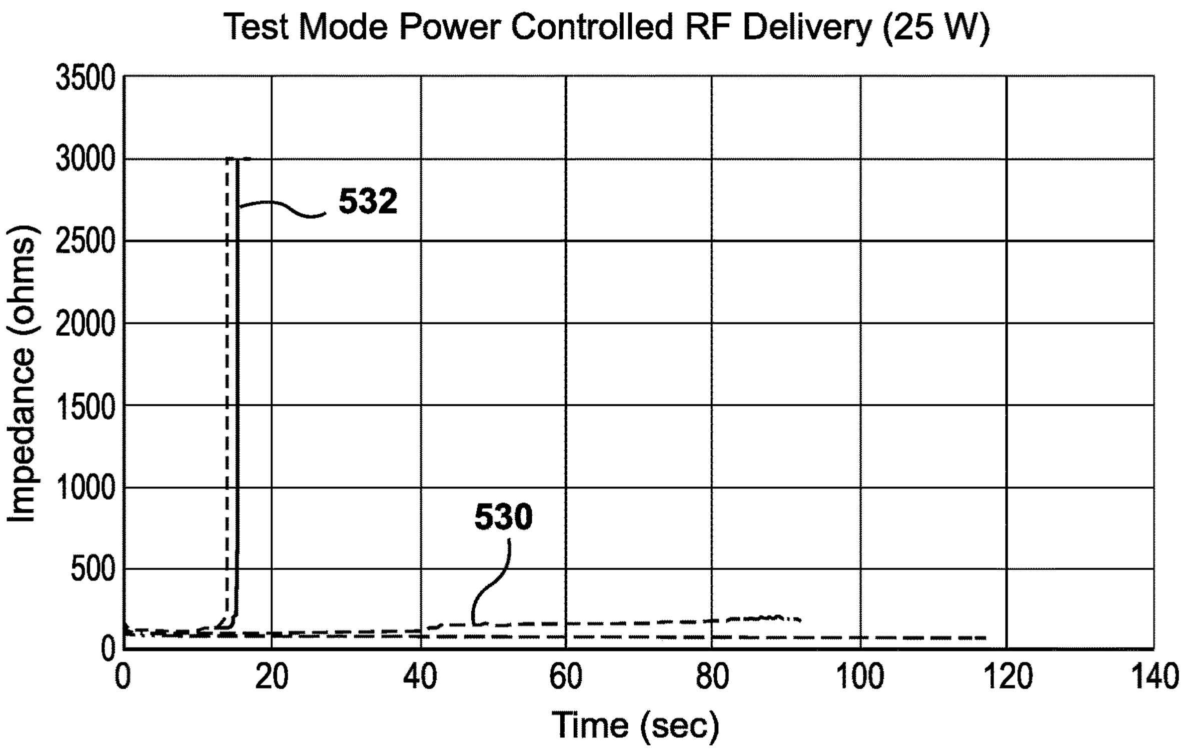
FIG. 17 illustrates an impedance graph measured during the delivery of energy.

In an alternate embodiment, a stimulus is imposed on the tissue prior to priming or ablating to measure the thermal and/or electrical characteristics of the tissue. In one embodiment, the tissue temperature is measured before and after the application of an RF bolus. The effective heat capacity is measured based on the energy input and the change in temperature of the tissue. In an alternate embodiment shown in FIG. 17, the tissue's impedance is measured during the delivery of an RF bolus. FIG. 17 shows the impedance of the tissue across time showing the tissue's reaction to an RF bolus. A low impedance 530 indicates the tissue is saturated or hydrated. A high impedance 532 indicates the tissue is desiccated or dry. A tissue with high impedance may be primed prior to ablation to improve the hydration of the tissue before the ablation procedure. In conjunction with or in the absence of tissue priming, a tissue with high impedance may require higher irrigation flow rates during the ablation procedure.

In another embodiment, the stimulus is cooling. Similarly, the tissue temperature is measured before and after the cooling process. In one embodiment, the cooling is applied for a known period of time t1. The tissue temperature T2 is measured after the completion of the cooling. The change in temperature between T2 and T1 is used to determine the tissue's thermal and/or electrical characteristics. Alternately, the cooling is applied until a predetermined temperature is reached. The time to reach the predetermined temperature is used to determine the tissue's thermal and/or electrical characteristics.

In a further embodiment, a stimulus such as RF energy is imposed on the tissue. The tissue temperature is measured after stimulus. After a known period of time, the tissue temperature is measured to determine the rate at which the tissue returns to normal body temperature. Alternatively, the second tissue measurement is taken at predetermined temperature (such as normal body temperature) and the time is measured. In alternate embodiments, a combination of stimuli is imposed on the tissue to determine the tissue's thermal and/or electrical characteristics.

In some embodiments, the tissue's thermal and/or electrical characteristics inform the physician if priming is needed prior to the ablation procedure. Furthermore, the tissue's thermal and/or electrical characteristics may influence the ablation parameters. In other words, the tissue's thermal and/or electrical characteristics are energy delivery parameters. For example, in tissues with a relatively high effective heat capacity, a greater amount of energy is delivered to create the desire ablation pattern. In tissues with a relatively low effective heat capacity, the fluid flow rate of the cooling fluid circulating through the probe may be increased to enhance thermal and electrical conductivity of the target tissue which will reduce the chance of impedance spikes and subsequent tissue charring.

Adjustment of the Amount of Cooling Fluid During Ablation Procedure

In accordance with an embodiment of the invention, the target tissue is cooled and irrigated during the ablation of the tissue. In one embodiment, the energy delivery device is the probe 100. As the fluid circulates through the probe 100, the probe 100 is cooled and the tissue is irrigated. As the flow rate is increased, the cooling and volume of ejected fluid is increased. Once the probe 100 and surrounding target tissue is cooled to the temperature of the circulating fluid, the ability to cool based on the flow rate plateaus. In other words, increasing the flow rate of the cooling fluid will not further decrease the probe's temperature. At this point, an increase of the fluid flow rate will continue to increase the irrigation while the cooling capabilities have plateaued. The increased irrigation hydrates the target tissue. The irrigation continuously hydrates the tissue during the ablation. The thermal and electrical characteristics of the tissue are modulated or altered due to the irrigation and hydration of the tissue. At the cooling plateaus, the flow rate can be controlled to achieve a desired irrigation rate to achieve the desired tissue characteristics while the internal probe cooling remains constant.

Figure 18:
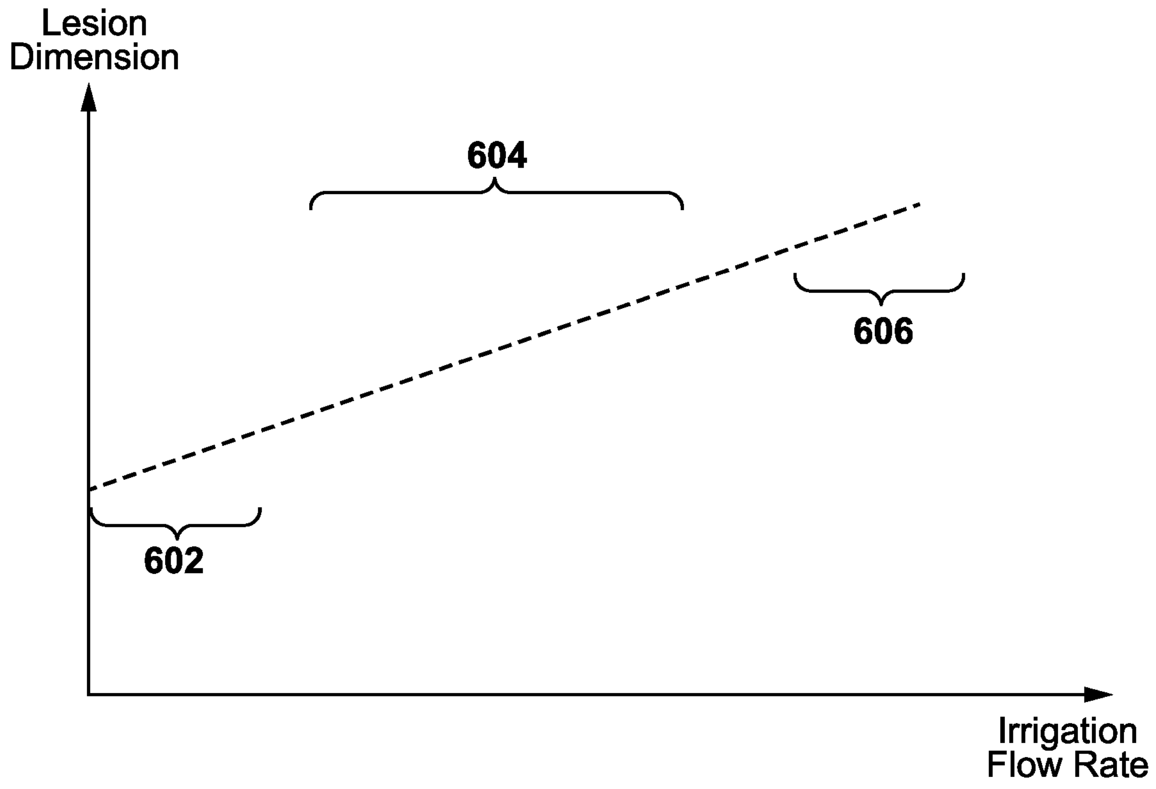
FIG. 18 illustrates the lesion dimension relative to the irrigation flow rate.

The irrigation flow rate may range between 0-100% of the probe flow rate. In other words, the irrigation flow rate may range between 0 mL/min and the probe flow rate (for example 50 ml/min). FIG. 18 demonstrates the relation between the irrigation flow rate and the lesion size. At low irrigation flow rates 602, the lesion dimension is equivalent to internally cooled probes having no irrigation. At medium irrigation flow rates 604, the lesion dimensions are consistent and larger than cooled probes having no irrigation. At high irrigation flow rates 606, large lesions are formed but are inconsistent and are prone to charring. In one embodiment, the irrigation flow rate of the probe 100 is between 0 and 3 mL/min. In an alternate embodiment, the irrigation flow rate of the probed 100 is between 0.3 and 0.8 mL/min. In a further embodiment, the irrigation flow rate of the probe 100 is between 0.4 and 0.6 mL/min.

Figure 19:
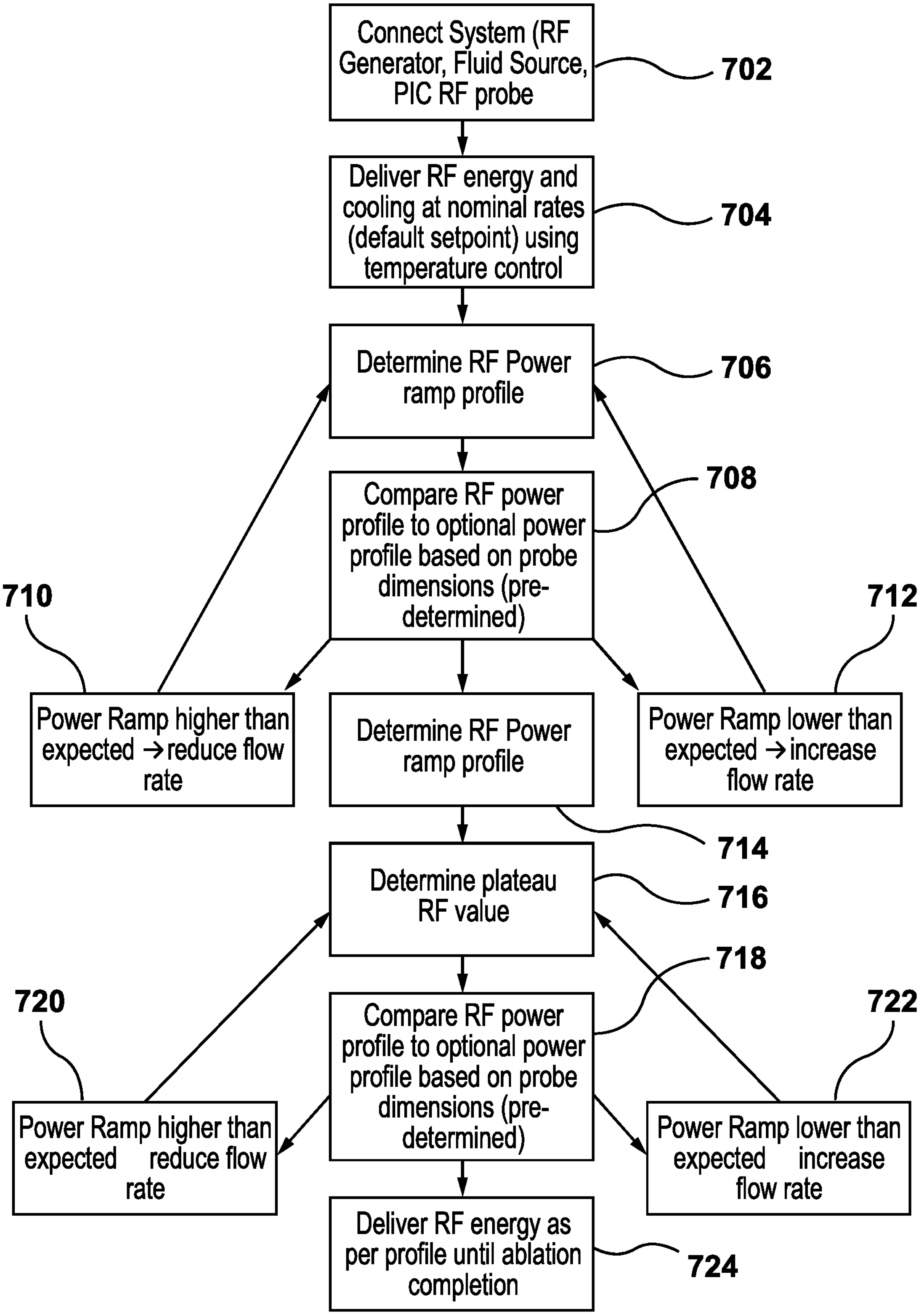
FIG. 19 is a flow chart showing a method in accordance with an embodiment of the present invention.

In the embodiment of FIG. 19, the flow rate of the cooling fluid is controlled based on the power profile of the ablation system. The power profile is the output of power in Watts over a period of time. The flow rate is adjusted to optimize the RF power ramp profile and the RF plateau value. Step 702 comprises connecting the probe 100 to an RF generator and a fluid source. The probe is positioned adjacent to the target tissue. When the probe is in the correct position, RF energy is delivered and the probe is cooled at nominal or standardized initial rates (step 704). During this step, the temperature is monitored. In such embodiments, the RF energy output to the target tissue varies with the measured temperature. The RF power ramp profile is determined by the temperature of the target tissue (step 706). In step 708, the RF power profile is compared to an optimal predetermined or pre-set power profile. The predetermined power profile can be based on the dimension of probe 100 in addition to the clinical data, patient history, etc. In an alternate embodiment, the outputs determined in step 706 is one or more of the following parameters, power ramp, peak power, current ramp, current peak, impedance or other parameters known in the art. The comparison of step 708 is based on the corresponding parameter measured in step 706.

If the RF power ramp profile is higher than the optimal power profile, the fluid flow rate of the cooling fluid is decreased (step 710). A decrease in fluid flow causes a lower fluid pressure within the probe, and therefore reduces the volume of fluid ejecting from the probe 100. The lower fluid flow rate results in less irrigation of the tissue. If the RF power ramp profile is lower than the optimal power profile, the fluid flow rate of the cooling fluid is increased (step 712). An increase in the fluid flow rate results in a higher pressure of fluid within the probe 100 resulting in an increased volume of fluid ejecting from the probe 100 into the target tissue. The higher fluid flow rate results in increased irrigation of the tissue and the tissue is further hydrated. The irrigated tissue results in a reduction in the measured temperature. The reduction in measured temperature in turn results in the RF generator increasing the power output to achieve the pre-determined temperature profile. In one embodiment, the RF power ramp profile is continuously compared to the predetermined optimal profile and the fluid flow of the probe 100 is continuously adjusted with the goal to achieve an RF power profile similar to the optimal power profile (steps 706-712).

Once the power ramp is completed (step 714), RF energy is delivered during the plateau region. The RF energy delivery through the plateau region is determined by the temperature of the target tissue. Step 716 comprises determining the plateau RF value. The plateau RF value is compared to an optimal predetermined or pre-set plateau profile (step 718). The optimal plateau profile is based on the probe dimensions. If the plateau RF value is higher than the optimal profile values, the fluid flow rate of the probe is reduced (step 720). A reduced fluid flow rate reduces the irrigation of the tissue. If the plateau RF value is lower than the optimal profile values, the fluid flow rate of the probed is increased (step 722). An increased fluid flow rate increases the irrigation of the tissue and the tissue is further hydrated. The fluid flow of the fluid circulating through the probe is continuously adjusted based on the plateau RF value until ablation is complete (step 724).

In an embodiment of the invention, the process of priming or irrigating the tissue prior to the ablation is combined with a continuous adjustment to the irrigation of the tissue during the ablation procedure. In other words, the methods of FIG. 15 are combined with the methods of FIG. 19. The combination provides optimized tissue thermal and electrical characteristic for the start of the ablation process as well as monitoring the tissue characteristics throughout the procedure and adjusting the ablation procedure accordingly.

Some embodiments may include an RF Ablation System including an RF Generator, RF Probe, Peristaltic Pump, RF Cable Hub, Probe Introducer Assembly, and Fluid Circulation Tubing. In one embodiment, a monopolar partially irrigated probe comprises a distal end size of 4-5.5 mm, with 1 or 2 holes with a hole diameter of 25-35 μm. The Test Media comprised of fresh chicken breast. Sample preparations included the chicken breast being placed in a water-tight pouch. The water-tight pouch was immersed into a 37° C. water bath for 30-60 minutes prior to testing to warm the tissue. Once the sample tissue reached 37° C., the sample tissue was placed on a tissue holder fixture. The probe was then placed within the sample tissue. A return electrode was placed at least 20 cm away from the distal end of the probe to allow for uniform distribution of current around the active tip and to create impedance values similar to what is observed in the human body.

Figure 20:
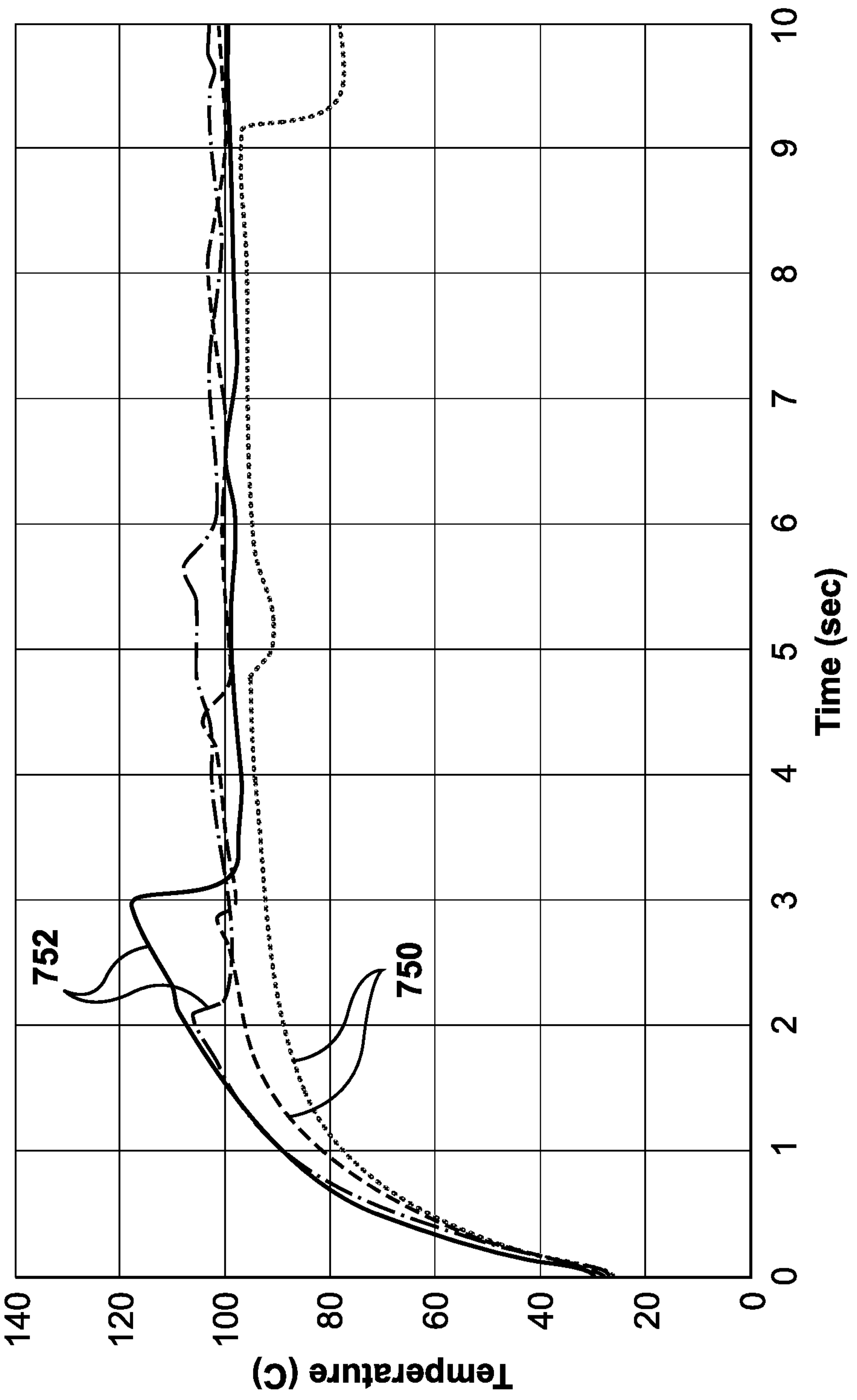
FIG. 20 is a temperature graph comparing a partially irrigated probe with an internally cooled probe.

FIG. 20 shows the temperature of the sample tissue from the delivery of a 25W of RF energy. The internal flow rates of the probes were 30 mL/min and the active tip lengths were 4 mm. The system utilized a power controlled setting. FIG. 20 shows the temperature change over time of a partially irrigated probe with a 1 mL/min irrigation flow rate 750 compared with a stock 4 mm cooled probe 752 (i.e. internal cooling with no irrigation). Both the partially irrigated probe 750 and the cooled probe 752 had an internal probe flow rate of 30 mL/min. Upon the delivery of the RF energy, the internally cooled probe 752 experiences a higher temperature than the partially irrigated probe 750. The high temperature experienced by the internally cooled probe 752 may lead to tissue charring.

Figure 21:
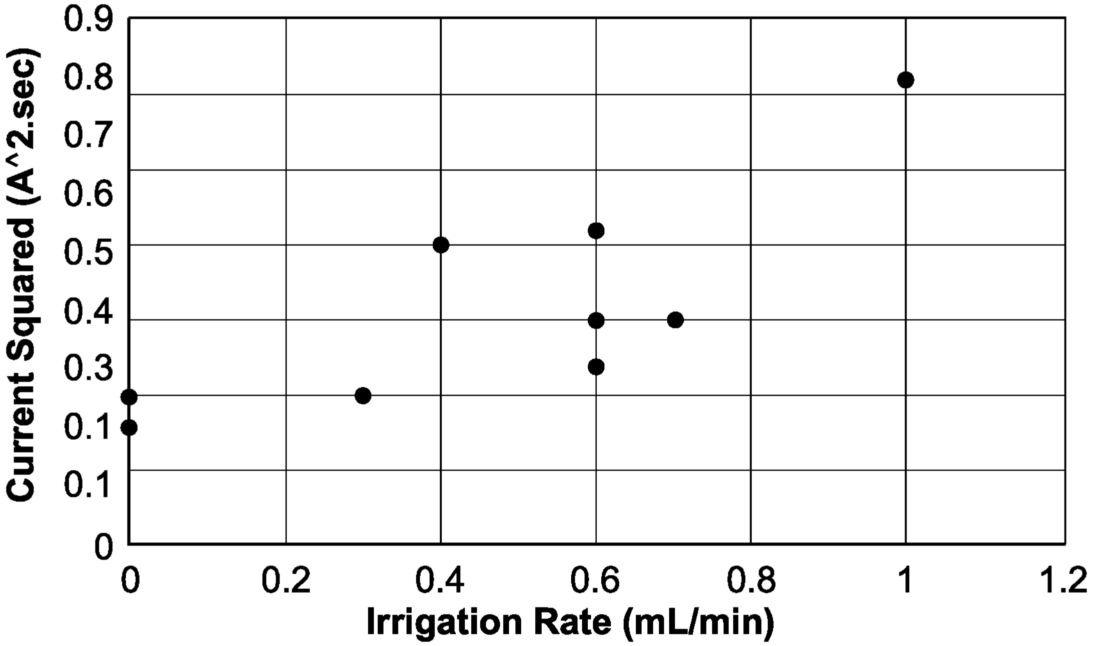
FIG. 21 is a graph showing the integration of current squared over time relative to the irrigation rate.
Figure 22:
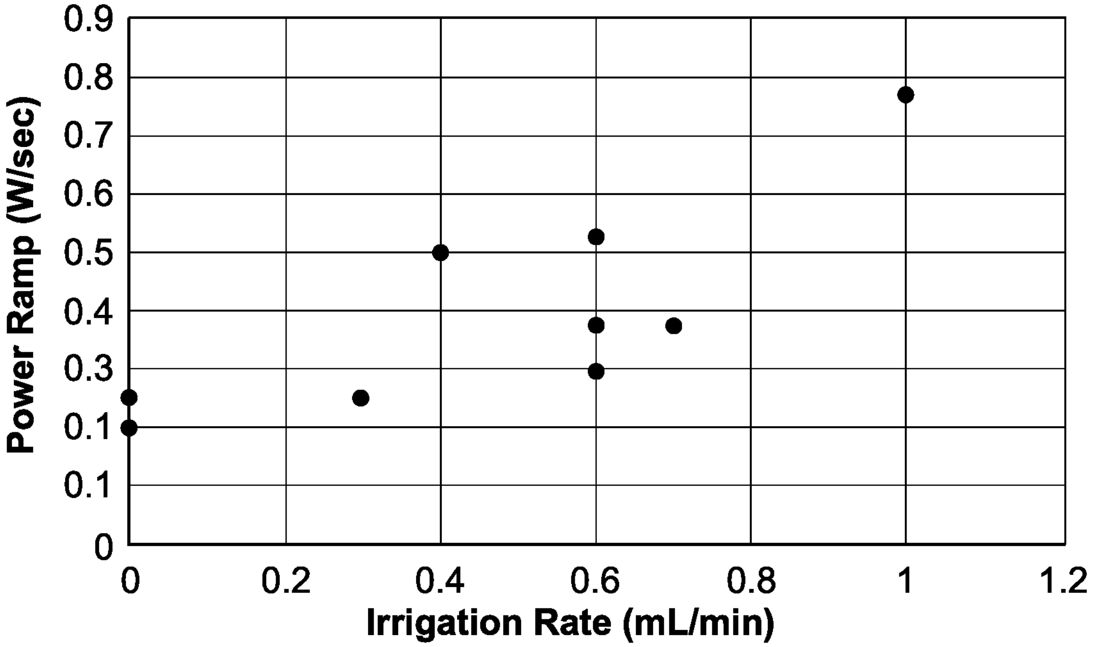
FIG. 22 is a graph showing the power ramp relative to the irrigation rate.

FIG. 21 shows the integration of current squared over time ($A^2$sec) relative to the irrigation flow rate (mL/min) of the irrigated probe. FIG. 22 shows the Power Ramp (W/sec) relative to the irrigation flow rate (mL/min) of the irrigated probe. FIGS. 21 and 22 show that when the irrigation rate increases, the system outputs more energy (power, current, etc.) and therefore the resulting lesions will be larger.

Figure 23:
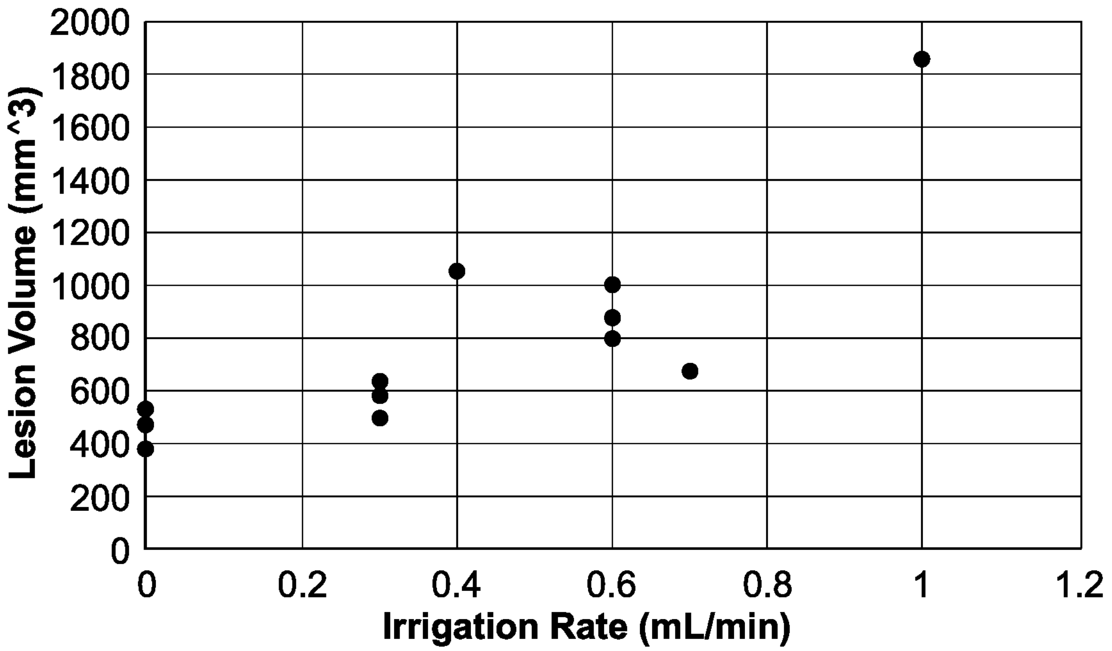
FIG. 23 is a graph showing the lesion volume relative to the irrigation rate.

FIG. 23 shows the lesion volume ($mm^3$) relative to the irrigation rate (mL/min). The lesion volume was determined by dissecting the sample tissue after the ablation was complete. Following the dissection, the length, (A), width (B) and depth (C) of the lesions were measured using a calibrated ruler. The volume was calculated using the ellipsoid formula, Volume=4/3*π*A*B*C. As seen in FIG. 23, the lesion volume increased as the irrigation rate increased. At low irrigation flow rates, the lesion dimension is similar to internally cooled probes having no irrigation. The increased irrigation causes a reduction in measured temperature (FIG. 20) which in turn results in the RF generator increasing the power output to achieve the pre-determined temperature profile. This increase in power output results in a larger lesion size.

FURTHER EXAMPLES

1) A probe for forming a lesion in a target tissue while delivering a cooling fluid, the probe comprising:
   - an elongate member comprising a distal tip and a proximal end, the elongate member defining a lumen therebetween, wherein the cooling fluid circulates through the lumen;
   - at least one active portion configured for delivering energy to the target tissue, positioned on the elongate member; and,
   - at least one orifice;
   - wherein the probe is configured such that a portion of the cooling fluid is ejected from the at least one orifice to cool the target tissue and a remainder of cooling fluid is internally circulated through the lumen.

2) The probe of example 1, wherein the elongate member is at least partially composed of a conductive material.

3) The probe of example 2, wherein the probe further comprises a layer of insulation covering the conductive material and the at least one active portion being electrically exposed.

4) The probe of example 1, wherein the elongate member is composed of a non-conductive material and the probe further comprises a wire for delivering energy to the at least one active portion.

5) The probe of any one of examples 1 to 4, wherein the at least one active portion includes at least one electrode.

6) The probe of any one of examples 1 to 5, wherein the at least one active portion is configured to deliver radiofrequency energy.

7) The probe of any one of examples 1 to 6, wherein the at least one active portion is located at the distal tip of the elongate member.

8) The probe of any one of examples 1 to 7, wherein the distal tip shape is selected from the group consisting of a dome tip, a blunt tip, a sharp tip, a sharp slanted tip, or a curved sharp tip.

9) The probe of any one of examples 1 to 8, wherein the distal tip further comprises a protrusion.

10) The probe of any one of examples 1 to 9, wherein the at least one active portion permits a measurement of impedance of the target tissue.

11) The probe of example 10, wherein the measurement of impedance is detected by a generator and wherein the generator adjusts energy delivery in response to the measurement of impedance.

12) The probe of any one of examples 1 to 11, wherein the probe is a monopolar probe, wherein the at least one active portion comprises a single active portion.

13) The probe of any one of examples 1 to 11, wherein the probe is a bipolar probe, wherein the at least on active portion comprises two active portions.

14) The probe of any one of examples 1 to 13, wherein the at least one orifice is on the at least one active portion.

15) The probe of example 14, wherein the at least one orifice is at a proximal portion of the at least one active portion.

16) The probe of example 14, wherein the at least one orifice is at a distal portion of the at least one active portion.

17) The probe of example 14, wherein the at least one orifice is at a lateral side of the electrode.

18) The probe of any one of examples 1 to 17, wherein the at least one orifice is formed by laser cutting.

19) The probe of any one of examples 1 to 17, wherein the at least one orifice is formed by drilling.

20) The probe of any one of examples 1 to 19, wherein the at least one orifice comprises a plurality of orifices.

21) The probe of example 20, wherein the plurality of orifices are distributed across the at least one active portion.

22) The probe of example 21, wherein the plurality of orifices are more concentrated in a proximal direction.

23) The probe of example 21, wherein the plurality of orifices are more concentrated in a distal direction.

24) The probe of example 21, wherein the plurality of orifices are concentrated at a region having a relatively higher levels of current density on the at least one active portion.

25) The probe of any one of examples 20 to 24, wherein the plurality of orifices have varying diameters.

26) The probe of any one of examples 1 to 25, wherein the at least one orifice is configured to eject the cooling fluid at an angle less than 90 degrees from an outer surface of the probe towards the distal tip.

27) The probe of any one of examples 1 to 25, wherein the at least one orifice is configured to eject the cooling fluid at an angle of less than 90 degrees from an outer surface of the probe towards the proximal end.

28) The probe of any one of examples 1 to 25, wherein the at least one orifice is tapered.

29) The probe of any one of examples 1 to 28, wherein the probe further comprises a temperature sensor.

30) The probe of example 29, wherein the temperature sensor is a thermocouple.

31) The probe of example 30, wherein the thermocouple is positioned within the lumen of the elongate member.

32) The probe of example 31, wherein the thermocouple is positioned at the distal tip of the elongate member.

33) The probe of example 30, wherein the thermocouple protrudes past the distal tip of the elongate member.

34) The probe of example 30, wherein the thermocouple is flush with a distal surface of the elongate member.

35) The probe of any one of examples 31 to 34, wherein the thermocouple is contained within a thermocouple lumen.

36) The probe of example 35, wherein the thermocouple lumen is composed of a conductive material.

37) The probe of example 35, wherein the thermocouple lumen is comprised of a non-conductive material.

38) The probe of any one of examples 31 to 37, wherein the thermocouple comprises two insulated wires, wherein each of the two insulated wires further comprise an exposed distal tip, and wherein contact of the two exposed distal tips form a junction.

39) The probe of any one of examples 31 to 38, wherein the thermocouple is electrically isolated.

40) The probe of example 36, wherein the thermocouple comprises a single insulated wire, wherein the single insulated wire further comprises an exposed distal tip, and wherein contact of the exposed distal tip and the thermocouple lumen form a junction.

41) The probe of any one of examples 30 to 40, wherein a radiofrequency generator detects a temperature measured by the temperature sensor and wherein the radiofrequency generator adjusts energy output in response to the temperature measured.

42) The probe of any one of examples 1 to 40, wherein the probe further comprises a pneumatic resistor, the pneumatic resistor is positioned within the lumen of the elongate member, adjacent the at least one orifice.

43) The probe of example 42, wherein the pneumatic resistor comprises a tube.

44) The probe of any one of examples 42 to 43, wherein the pneumatic resistor is attached to a surface of the lumen at the distal tip of the probe.

45) The probe of example 44, wherein the pneumatic resistor is attached using an adhesive.

46) The probe of example 44, wherein the pneumatic resistor is attached by laser welding.

47) The probe of any one of examples 42 to 46, wherein the pneumatic resistor comprises a cross-section selected from the group consisting of a circle, square, or rectangle.

48) The probe of example 47, wherein the cross-section varies along a length of the pneumatic resistor.

49) The probe of example 48, wherein the cross-section tapers from a first size to a second size.

50) The probe of any one of examples 1 to 49, wherein the probe further comprises an inlet lumen and an outlet lumen, wherein the cooling fluid flow into the probe through the inlet lumen and exits the probe through the outlet lumen.

51) The probe of any one of examples 1 to 50, wherein the cooling fluid comprises bubbles whereby the cooling fluid can be visualized using an ultrasound visualization system.

52) The probe of any one of examples 1 to 51, wherein the cooling fluid comprises a contrast agent whereby the cooling fluid can be visualized using a fluoroscopy visualization system.

53) The probe of any one of examples 1 to 52, wherein the proximal end of the elongate member is configured to connect to a radiofrequency generator and a cooling pump.

54) A probe for forming a lesion in a target tissue while delivering a cooling fluid, the probe comprising:

an elongate member comprising a distal tip and a proximal end;

a protrusion protruding from the distal tip;

a lumen extending between the proximal end of the elongate member and the protrusion, wherein a cooling fluid circulates through the lumen;

at least one active portion configured for delivering energy to the target tissue; and, at least one orifice;

whereby a portion of the cooling fluid is ejected from the at least one orifice to cool the target tissue and a remainder of cooling fluid is circulated through the lumen.

55) The probe of example 54, wherein the protrusion is in fluid communication with the lumen via a hole.

56) The probe of any one of examples 54 to 55, wherein the at least one orifice is on the protrusion.

57) The probe of any one of examples 54 to 56, wherein the protrusion comprises a non-conductive portion and further comprises a conductive portion.

58) The probe of any one of examples 54 to 56, wherein the protrusion is composed of a conductive material.

59) The probe of any one of examples 54 to 58, wherein the protrusion is selected from the group consisting of a dome tip, a blunt tip, a sharp tip, a sharp slanted tip, or a curved slanted tip.

60) The probe of any one of examples 54 to 59, wherein the probe further comprises a temperature sensor.

61) The probe of example 60, wherein the temperature sensor is positioned within the protrusion.

62) The probe of example 61, wherein the temperature sensor is a thermocouple.

63) The probe of example 62, wherein the thermocouple is contained within a thermocouple lumen.

64) The probe of any one of examples 62 to 63, wherein the thermocouple lumen is composed of a conductive material.

65) The probe of any one of examples 62 to 64, wherein the thermocouple lumen is composed of a non-conductive material.

66) The probe of any one of examples 62 to 65, wherein the thermocouple comprises two insulated wires wherein each of the two insulated wires further comprise an exposed distal tip, and wherein contact of the two exposed distal tips form a junction.

67) The probe of any one of examples 62 to 66, wherein the thermocouple is electrically isolated.

68) The probe of example 64, wherein the thermocouple comprises a single insulated wire, wherein the single insulated wire further comprises an exposed distal tip, and wherein contact of the exposed distal tip and the thermocouple lumen form a junction.

69) The probe of any one of example 60 to 69, wherein a radiofrequency generator detects a temperature measured by the temperature sensor and wherein the radiofrequency generator adjusts energy output in response to the temperature measured.

70) A system for forming a lesion in a target tissue, the system comprising:
a probe of any one of examples 1 to 69;
a cooling pump configured to deliver the cooling fluid to the probe; and,
a generator configured to deliver energy to the probe.

71) The system of example 70, wherein the generator is a radiofrequency generator.

72) The system of any one of examples 70 to 71, wherein the cooling pump adjusts a flow rate in response to a tissue characteristic.

73) The system of example 72, wherein the tissue characteristic is a temperature of the target tissue.

74) The system of example 72, wherein the tissue characteristic is an impedance of the target tissue.

75) The system of any one of examples 70 to 71, wherein the generator adjusts the delivery of energy in response to a tissue characteristic.

76) The system of example 75, wherein the tissue characteristic is a temperature of the target tissue.

77) The system of example 75, wherein the tissue characteristic is an impedance of the target tissue.

78) A method of lesioning a target tissue, the method comprising the steps of: inserting the probe of any one of examples 1 to 69 into a patient;
positioning the at least active portion at the target tissue;
delivering energy to form a lesion; and,
delivering the portion of the cooling fluid to the target tissue.

79) The method of example 78, wherein the method further comprises a step of measuring a tissue characteristic and adjusting the delivery of energy based on the tissue characteristic.

80) The method of example 79, wherein the step of measuring the tissue characteristic comprises measuring a temperature of the target tissue.

81) The method of example 79, wherein the step of measuring the tissue characteristic comprises measuring an impedance of the target tissue.

82) The method of example 78, wherein the method further comprises a step of measuring a tissue characteristic and adjusting a flow rate of the cooling fluid based on the tissue characteristic.

83) The method of example 82, wherein the step of measuring the tissue characteristic comprises measuring a temperature of the target tissue.

84) The method of example 82, wherein the step of measuring the tissue characteristic comprises measuring an impedance of the target tissue.

85) A method of delivering energy to a region of tissue within a patient's body using a medical treatment system, said medical treatment system comprising an energy delivery device comprising a lumen for circulating fluid at a flow rate and at least one orifice, coupled to an energy source and a fluid source, the method comprising the steps of:
delivering energy through the energy delivery device; and
circulating fluid through the lumen of the energy delivery device, wherein a portion of the fluid is ejected from the at least one orifice;

86) The method of example 85, further comprising the steps of:
monitoring an energy delivery parameter associated with the delivery of energy by the medical treatment system; and
comparing the energy delivery parameter to a predetermined energy delivery parameter.

87) The method of example 86, further comprising the step of controlling the flow rate of the circulating fluid based on the energy delivery parameter.

88) The method of any one of examples 85 to 86, further comprising the step of controlling the energy delivery based on the energy delivery parameter.

89) The method of example 85, further comprising the steps of:
determining an RF power ramp profile of the energy delivery device;
comparing the RF power profile to a predetermined RF power profile; and
controlling the flow rate of the circulating fluid based on the RF power ramp profile.

90) The method of example 89, wherein the flow rate is increased when the RF power ramp profile is lower than the predetermined RF power profile.

91) The method of example 89, wherein the flow rate is decreased when the RF power ramp profile is higher than the predetermined RF power profile.

92) The method of any one of examples 89 to 91, further comprising the steps:
determining the plateau RF value of the energy delivery device;
comparing the plateau RF value to a predetermined plateau RF value; and
controlling the flow rate of the circulating fluid based on the plateau RF value.

93) The method of example 92, wherein the flow rate is increased when the plateau RF value is lower than the predetermined plateau RF value.

94) The method of example 92, wherein the flow rate is decreased when the plateau RF value is higher than the predetermined plateau RF value.

95) A method of delivering energy to a region of tissue within a patient's body using a medical treatment system, said medical treatment system comprising an energy delivery device comprising a lumen for circulating fluid at a flow rate and at least one orifice, coupled to an energy source and a fluid source, the method comprising the steps of:
stimulating the region of tissue;
monitoring an energy delivery parameter associated with the delivery of energy by the medical treatment system;
comparing the energy delivery parameter to a predetermined energy delivery parameter; and
delivering energy through the energy delivery device.

96) The method of example 95, wherein the step of stimulating the region of tissue comprises at least one stimulus.

97) The method of example 96, wherein the at least one stimulus is an energy bolus.

98) The method of example 96, wherein the at least one stimulus is partially irrigated cooling.

99) The method of example 96, wherein at least one stimulus is internal cooling.

100) The method of example 96, wherein the at least one stimulus comprises two stimuli comprising an energy bolus and partially irrigated cooling.

101) The method of example 95, wherein the step of stimulating the region of tissue comprises:
cooling the energy deliver device and irrigating the region of tissue for a known period of time.

102) The method of example 95, wherein the step of stimulating the region of tissue comprises:
cooling the energy deliver device and irrigating the region of tissue until a desired temperature of the region of tissue is reached.

103) The method of example 95, wherein the step of stimulating the region of tissue comprises:
delivering an energy bolus to the region of tissue.

104) The method of any one of examples 95 to 103, wherein the energy delivery parameter is impedance.

105) The method of any one of examples 95 to 103, wherein the energy delivery parameter is effective heat capacitance.

106) The method of any one of examples 95 to 103, wherein the energy delivery parameter is temperature.

107) The method of any one of examples 95 to 103, wherein the step of monitoring an energy delivery parameter comprises:
measuring a first temperature of the region of tissue prior to the step of stimulating the region of tissue; and
measuring a second temperature of the region of tissue after the step of stimulating the region of tissue.

108) The method of example 107, wherein the step of monitoring an energy delivery parameter further comprises measuring a third temperature of the region of tissue after a predetermined amount of time.

109) The method of any one of examples 95 to 103, wherein the step of monitoring an energy delivery parameter comprises:
measuring a first temperature of the region of tissue after the step of stimulating the region of tissue; and
measuring a second temperature of the region of tissue after a predetermined amount of time.

110) The method of any one of examples 95 to 103, wherein the step of monitoring an energy delivery parameter comprises:
measuring a first temperature of the region of tissue after the step of stimulating the region of tissue; and
measuring the time elapsed until a desired temperature of the region of tissue is reached.

111) The method of any one of examples 95 to 110, further comprising determining the effective heat capacity of the region of tissue.

112) The method of any one of examples 95 to 111, further comprising the step of stimulating the region of tissue with a second stimulus.

113) The method of example 95, wherein the step of delivering energy comprises the steps of any one of example 85 to 94.

114) The method of example 111, wherein an additional RF bolus is delivered when the effective heat capacity is higher than the predetermined value.

115) The method of example 111, wherein the region of tissue is cooled for the known period of time when the effective heat capacity is lower than the predetermined value.

116) The method of any one of examples 85 to 115, further comprising the step of delivering RF energy until ablation is completed.

117) The method of any one of examples 85 to 116, wherein the energy delivery device is the probe of any one of examples 1 to 69.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method of delivering energy to a region of tissue within a patient's body using a medical treatment system, said medical treatment system comprising an energy delivery device comprising a lumen for circulating fluid at a flow rate and at least one orifice, coupled to an energy source and a fluid source, the method comprising the steps of:
delivering energy through the energy delivery device;
circulating fluid through the lumen of the energy delivery device, wherein a portion of the fluid is ejected from the at least one orifice;
determining a radiofrequency power profile of the energy delivery device;
comparing the radiofrequency power profile to a predetermined radiofrequency power profile; and
controlling the flow rate of the circulating fluid based on the step of comparing the radiofrequency power profile.

2. The method of claim 1, wherein when the radiofrequency power profile is lower than the predetermined radiofrequency power profile, the flow rate of the circulating fluid is increased.

3. The method of claim 1, wherein when the radiofrequency power profile is higher than the predetermined radiofrequency power profile, the flow rate of the circulating fluid is decreased.

4. The method of claim 1, wherein the radiofrequency power profile comprises a radiofrequency power ramp profile.

5. The method of claim 1, wherein the radiofrequency power profile comprises a plateau radiofrequency value.

6. The method of claim 1, wherein the radiofrequency power profile comprises a radiofrequency power ramp profile and a plateau radiofrequency value, and wherein the step of comparing the radiofrequency power profile to the predetermined radiofrequency power profile comprises one or both of comparing the radiofrequency power ramp profile to a predetermined radiofrequency power ramp profile, and comparing the plateau radiofrequency value to a predetermined plateau radiofrequency value.

7. The method of claim 1, wherein the steps of determining the radiofrequency power profile, comparing the radiofrequency power profile, and controlling the flow rate, are repeated at least once throughout a procedure.

8. The method of claim 7, wherein the radiofrequency power profile is substantially continuously compared to the predetermined radiofrequency power profile, and wherein the flow rate of the circulating fluid is substantially continuously adjusted for achieving a radiofrequency power profile similar to the predetermined radiofrequency power profile.

* * * * *